(12) United States Patent
Shurygin et al.

(10) Patent No.: US 10,493,164 B2
(45) Date of Patent: Dec. 3, 2019

(54) METHOD FOR PREVENTING AND TREATING ADHESIONS

(71) Applicant: Joint Stock Company "Pharmasyntez", Irkutsk (RU)

(72) Inventors: Mikhail Gennadievich Shurygin, Irkutsk (RU); Irina Aleksandrovna Shurygina, Irkutsk (RU)

(73) Assignee: Joint Stock Company "PHARMASYNTEZ" (RU)

( * ) Notice: Subject to any disclaimer, the term of this patent is extended or adjusted under 35 U.S.C. 154(b) by 0 days.

(21) Appl. No.: 16/225,987

(22) Filed: Dec. 19, 2018

(65) Prior Publication Data
US 2019/0125886 A1    May 2, 2019

Related U.S. Application Data

(60) Division of application No. 14/082,947, filed on Nov. 18, 2013, now Pat. No. 10,172,952, which is a continuation-in-part of application No. PCT/IB2012/052483, filed on May 17, 2012.

(30) Foreign Application Priority Data

May 17, 2011  (RU) ................................. 2011119848
Dec. 26, 2011  (RU) ................................. 2011153043

(51) Int. Cl.
*A61K 47/58*     (2017.01)
*C07D 401/04*    (2006.01)
*C08G 73/02*     (2006.01)

(52) U.S. Cl.
CPC ............ *A61K 47/58* (2017.08); *C07D 401/04* (2013.01); *C08G 73/0206* (2013.01)

(58) Field of Classification Search
CPC .......... A61K 47/48176; A61K 47/4823; C07D 401/04; C08G 73/0206
USPC ............ 424/78.22; 514/55, 57; 525/276, 20; 536/31
See application file for complete search history.

(56) References Cited

U.S. PATENT DOCUMENTS

| | | | |
|---|---|---|---|
| 5,837,719 A | 11/1998 | de Laszlo et al. | |
| 5,894,971 A | 4/1999 | Huang | |
| 8,205,286 B1 | 6/2012 | Diaz | |
| 2010/0291055 A1 | 11/2010 | Athanasiadis et al. | |
| 2014/0259423 A1 | 9/2014 | Falck | |

FOREIGN PATENT DOCUMENTS

| | | |
|---|---|---|
| RU | 2363476 C1 | 10/2009 |
| WO | 199503297 | 2/1995 |
| WO | 0160868 A1 | 8/2001 |
| WO | 2004005264 A2 | 1/2004 |
| WO | 2009103821 A3 | 8/2009 |

OTHER PUBLICATIONS

Badger, Alison M. et al. Pharmacological Profile of SB 203580, a Selective Inhibitor of Cytokine Suppressive Binding Protein/p38 Kinase, in Animal Models of Arthritis, Bone Resorption, Endotoxin Shock and Immune Function. J. Pharmacol. Exp. Ther., 1996. vol. 279. No. 3, pp. 1453-1461.

Bennett, Steven L. et al. Next-Generation HydroGel Films as Tissue Sealants and Adhesion Barriers. J. Card. Surg., 2003. vol. 18, pp. 494-499.

Burlev, et al., Peritoneal adhesions: pathogenesis to prevention. Reproductive disorders, 2009. No. 3, pp. 36-44.

DiZerega, G.S. Contemporary adhesion prevention. Fertil. Steril., Feb. 1994. vol. 61, No. 2, pp. 219-235.

Diamond, Michael P. et al., Synergistic effects of Interceed (TC7) and heparin in reducing adhesion formation in the rabbit uterine horn model. Fertil. Sterit, Feb. 1991. vol. 55, No. 2, pp. 389-394.

DiZerega G.S. Peritoneum, Peritoneal Healing and Adhesion Formation. Perotoneal Surgery. Springer Science + Business Media New York, 2000. pp. 3-37.

Falabella & Chen, Cross-Linked Hyaluronic Acid Films to Reduce Intra-Abdominal Postsurgical Adhesions in an Experimental Model. Dig. Surg., 2009. vol. 26, pp. 476-481.

Gutmann & Diamond, Principles of laparoscopic microsurgery and adhesion prevention. Practical Manual of Operative Laparoscopy and Hysteroscopy: Ed. Azziz R., Murphy A.A.—New York: Springer, 1992. pp. 55-64.

De laco, Pier Andreaet al. A novel hyaluronan-based gel in laparoscopic adhesion prevention: preclinical evaluation in an animal model. Fertil. Steril., Feb. 1998. vol. 69, No. 2, pp. 318-323.

Pressato, Daniele et al. Hyaluronan derivatives in postsurgical adhesion prevention. Hyaluronan: Proceedings of an International Meeting, Sep. 2000, North East Wales Institute, UK, Woodhead Publishing, Cambridge, England, 2002, pp. 491-499.

Shurygina, I.A. et al., Influence of p38 MAPK inhibitor on inflammation after surgical wound. OzBio2010 Combined Conference, Melbourne, 2010, p. 230.

Tulandi, Togas. Adhesion Prevention in Laparoscopic Surgery. Int. J. Fertil. Menopausal. Stud.—1996.—vol. 41, No. 5,—pp. 452-457.

The Surgical Membrane Study Group: Prophylaxis of pelvic sidewall adhesions with Gore-Tex surgical membrane: a multicentre clinical investigation. Fertil. Steril., 1992. vol. 57. No. 4, pp. 921-923.

(Continued)

*Primary Examiner* — Johann R Richter
*Assistant Examiner* — Courtney A Brown
(74) *Attorney, Agent, or Firm* — Michele L. Lawson; Smith & Hopen, P.A.

(57) ABSTRACT

The invention relates to inhibitory compounds of a p38 MAP kinase having a structure of type (I)-(VII) which can be used for the treatment or prophylaxis of adhesion. Pharmaceutical compositions are disclosed containing an effective amount of the substance SB203580 or one or more of the conjugated compounds of type (I)-(VII) or a combination thereof, and a pharmaceutically acceptable carrier, a diluent or an excipient. Also disclosed is the use of the substance SB203580 as an agent having anti-adhesion activity. Also disclosed is a method for the prophylaxis and/or treatment of a disease or a condition in which there is a possibility of the formation and/or growth of adhesions, which makes it possible to dispense with the additional administration of a preparation in the post-operative period.

19 Claims, 9 Drawing Sheets

(56) References Cited

OTHER PUBLICATIONS

Zelenin, et al., Zazhivlenie khirugicheskoy rany v uslovyakh podavleniya aktivnosti r38 MAR-kinaznogo kaskada. Materialy 68-I otkrytoy nauchno-prakticheskoy konferentsii molodykh uchenykh I studentov s mezhdunarodnym uchatstiem, posvyaschennoy 75-letiyu VoIGMU, aktualnye problem eksperimentalnoy I klinecheskoy medistiny:, Sep. 9-13, 2010, Volograd, izdatelstvo VoIGMU, pp. 105-106.

International Search Report issued by the International Searching Authority dated Sep. 6, 2012 for international application No. PCT/IB2012/052483.

International Preliminary Report on Patentability issued by the International Bureau dated Nov. 17, 2013 for international patent application No. PCT/IB2012/052483.

Tulandi, Togas. Intraperitoneal instillates. Infertil. Reprod. Med. Clin. North. Am.—Jul. 1994.—vol. 5., No. 3 pp. 479-483.

METHOD FOR PREVENTING AND TREATING ADHESIONS

CROSS REFERENCE TO RELATED APPLICATIONS

This application is a divisional application of and claims priority to U.S. patent application Ser. No. 14/082,947, entitled "Compounds for adhesion treatment and prevention, compound-related pharmaceutical compositions and methods for the prevention and treatment of adhesions," filed on Nov. 18, 2013, which is a continuation-in-part application of and claims priority to PCT Application PCT/IB2012/052483, entitled "Compounds for Adhesion Treatment and Prevention, Compound-Related Pharmaceutical Compositions and Methods of the Prevention and Treatment of Adhesions," filed on May 17, 2012, which claims priority to Russian Patent Application No. RU2011119848, filed on May 17, 2011, and Russian Patent Application No. RU2011153043, filed on Dec. 26, 2011, the contents of each of which are herein incorporated by reference.

FIELD OF THE INVENTION

The technical field of the present application relates to the fields of pharmacy, clinical and experimental medicine and veterinary science. In particular, it relates to new compounds for the treatment and prevention of adhesions, pharmaceutical compositions containing these compounds, and to a method for the treatment and prevention of adhesion formation. Compounds described in this invention show inhibiting effects on p38 MAP-kinase.

BACKGROUND OF THE INVENTION

Adhesion formation is a topical problem of clinical medicine. Since adhesions often inhibit normal movement of tissues, including organs, it is considered as a serious complication after surgery. The incidence of intraperitoneal adhesions ranges from 67% to 93% after general surgical abdominal operations and up to 97% after open gynecological pelvic procedures.

It has been estimated that in the United States, there are 117 hospitalizations for adhesion-related problems per 100,000 people, and the total cost for hospital and surgical expenditure is about S1.3 billion [Abdominal adhesiolysis: inpatient care and expenditures in the United States in 1994/N. F. Ray, W. G. Denton, M. Thamer et al.//J. Am. Coll. Surg.—1998.—Vol. 186.—P. 1-9].

The main approaches in preventing adhesions include adjusting surgical techniques, limiting trauma to intra-abdominal structures, and applying adjuvants to decrease adhesion formation [Risberg B. O. Adhesions: Preventive strategies/B. O. Risberg//Eur. J. Surg. Suppl.—1997.—Vol. 577.—P. 32-39].

However, the use of some medicinal preparations for the prevention of adhesions is limited by the following factors:

Ischemic zones are at risk of adhesion formation, but they are distant from blood flow and thus from pharmacological effects of medications administered by common routes (per os, intravenously, intramuscularly, etc.);

1) An extremely rapid absorption mechanism which is typical for the peritoneal membrane affects the elimination half-life and efficacy of many medicinal agents administered intraperitoneally;

2) Any anti-adhesion agent should show its specific activity against the adhesion formation but not the normal wound repair which is necessary for adequate surgical treatment.

Intra-peritoneal thrombokinase, fibrinolysin, streptokinase, urokinase, hyaluronidase, chymotrypsin, trypsin, papain, and pepsin act directly by breakdown of the fibrinous mass and indirectly by stimulating plasminogen activator activity. The use of these agents is still awaiting appropriate human clinical trials [Alpay Z. Postoperative adhesions: from formation to prevention/Z. Alpay, G. M. Saed, M. P. Diamond//Semin. Reprod. Med.—2008.—Vol. 26, N 4.—P. 313-321].

The use of non-steroidal anti-inflammatory agents, glucocorticosteroids and antihistamines, progesterone/estrogen, anticoagulants, fibrinolytics, and antibiotics has not been found very effective in reducing adhesions and has been associated with an inadequate safety profile and a high incidence of various side effects [Pathogenesis, consequences, and control of peritoneal adhesions in gynaecologic surgery/Practice committee of the American society for reproductive medicine, The society of reproductive surgeons//Feral. Steril.—2008.—Vol. 90, Suppl. 5.—S. 144-149].

A pathologically justified approach to the prevention of adhesions is the use of methods and agents preventing approximation and adhesion of injured abdominal surfaces [Davey A. K. Surgical adhesions: A timely update, a great challenge for the future/A. K. Davey, P. J. Maher//J. of Minimally Invasive Gynecology.—2007.—Vol. 14.—P. 15-22].

An ideal barrier showing a high safety and efficacy profile should be noninflammatory, nonimmunogenic, and persist during the critical remestheliazation phase, staying in place without sutures or staples, and furthermore remain active in the presence of blood and be completely degradable. In addition, it should neither interfere with healing, promote infection and oncological process, nor itself cause adhesions [Yeo Y. Polymers in the prevention of peritoneal adhesions/ Y. Yeo, D. S. Kohane//European. J. of Pharmaceutics and Biopharmaceutics.—2008.—Vol. 68.—P. 57-66].

Nowadays, polymer solutions, solid membranes, precasted or in situ hydrogels are used as these barriers preventing adhesion formation. [Falabella C. A. Cross-linked hyaluronic acid films to reduce intra-abdominal postsurgical adhesions in an experimental model/C. A. Falabella, W. Chen//Dig. Surg.—. 2009.—Vol. 26, N 6.—P. 476-481; Hyaluronan derivatives in postsurgical adhesion prevention/ D. Pressato, E. Bigon, M. Dona et al.//in: Hyaluronan: Proceedings of an International Meeting, September 2000, North East Wales Institute, UK, Woodhead Publishing, Cambridge, England, 2002.—P. 491-499; A novel hyaluronan-based gel in laparoscopic adhesion prevention: preclinical evaluation in an animal model/P. A. D. Laco, M. Stefanetti, D. Pressato et al.//Fertil. Steril.—1998.—Vol. 69.—P. 318-323; hydrogels Next-generation hydrogel films as tissue sealants and adhesion barriers/S. L. Bennett, D. A. Melanson, D. F. Torchiana et al.//J. Card. Surg.—2003.—Vol. 18.—P. 494-499].

The use of crystalloid solutions for long-term separation of abdominal layers has been found inappropriate due to the rapid absorption of water and electrolytes from peritoneal cavity, with up to 500 ml of iso-osmolar sodium chloride absorbed in less than 24 hours in humans [Kinetics of peritoneal fluid absorption in adult man/L. Shear, C. Swartz, J. Shinaberger et al.//N. Engl. J. Med.—1965.—Vol. 272.—P. 123-127]. Because it takes 5 to 8 days for peritoneal surfaces to remesothelialize, a crystalloid solution should be absorbed well before the process of fibrin deposition and adhesion formation are complete. Clinical studies showed an adhesion re-formation rate of approximately 80% in patients who received crystalloid solutions [De Cherney A. H. Clinical problem of intraperitoneal postsurgical adhesion formation following general surgery and the use of adhesion prevention barriers/A. H. De Cherney, G. S di Zerega//Surg. Clin. North. Am.—1997.—Vol. 77.—P. 671-688].

Attempts have been made to use different polymer materials, in particular polymers of glucose (Dextran 70, isodextrin), carboxymethyl cellulose, and hyaluronic acid.

Dextran 70 (32% dextran 70 (Hyskon, Pharmacia, Sweden)) is a frequently used solution for adhesion prevention. Its main characteristics are as follows: dextran is slowly absorbed and draws fluid into the abdominal cavity. It also decreases clot formation [Gutmann J. N. Principles of laparoscopic microsurgery and adhesion prevention/J. N. Gutmann, M. P. Diamond//in: Practical Manual of Operative Laparoscopy and Hysteroscopy: Ed. Azziz R., Murphy A. A.—New York: Springer, 1992.—P. 55-64]. Follow-up studies of the initial observation did not show a reduction in adhesions. Moreover, significant side effects, such as ascites, weight gain, pleural effusion, labial edema, liver function abnormalities, and, albeit rare, disseminated intravascular coagulation and anaphylaxis, were noted, and dextran solution is used very rarely now. [di Zerega G. S. Contemporary adhesion prevention/G. S. di Zerega//Fertil. Steril.—1994.—Vol. 61.—P. 219-235]. The results have been inconsistent [Tulandi T. Intraperitoneal instillates/T. Tulandi// Infertil. Reprod. Med. Clin. North. Am.—1994.—Vol. 5.—P. 479-483].

Difficulties have been found in using porous polytetrafluoroethylene membranes as local barriers due to the formation of pseudocapsules [The Surgical Membrane Study Group: Prophylaxis of pelvic sidewall adhesions with Gore-Tex surgical membrane: A multicentre clinical investigation//Fertil. Steril.—1992.—Vol. 57.—P. 921-923]. Moreover, it has been technically difficult to use this material in laparoscopic surgery [Tulandi T. Adhesion prevention in laparoscopic surgery/T. Tulandi//Int. J. Fertil. Menopausal. Stud.—1996.—Vol. 41.—P. 452-457]. It requires a physical fixation and is not degradable. Therefore, it should be left or surgically removed later. Removal procedures may cause surgical traumas and lead to adhesion formation. These technical difficulties and usability problems have made the medication unpopular, and it is used very rarely now.

Oxidized regenerated cellulose (Interceed) is the only adjuvant approved for the specific purposes of postsurgical adhesion prevention. ORC appears to decrease adhesion formation-reformation beyond that achieved with meticulous surgical technique. ORC reduces both raw surface area and the occurrence of adhesion formation-reformation by a margin of 20% [Interceed (TC7) Adhesions Barrier Study Group: Prevention of postsurgical adhesions by Interceed (TC7), an absorbable adhesion barrier: A prospective, randomized multicenter clinical study//Fertil. Steril.—1989.— Vol. 51.—P. 933-938]. When applied to a raw peritoneal surface, it becomes gel within 8 hours [Synergistic effects of Interceed (TC7) and heparin in reducing adhesion formation in the rabbit uterine horn model/M. P. Diamond, C. B. Linsky, T. Cunningham et al.//Fertil. Steril.—1991.—Vol. 55.—P. 389-394]. ORC can be applied easily by laparoscopy and does not need suturing. However, clinical observation indicates that small amounts of bleeding at the time that ORC is applied results in blood permeating the weave of the material. Fibroblasts grow along the strands of clotted blood with subsequent collagen deposition and vascular proliferation [Frankfurter D. Pelvic adhesive disease/D. Frankfurter, A. H. De Cherney//Postgrade Obstet. Gynecol.—1996.— Vol. 16.—P. 1-5]. This means that the presence of intraperitoneal blood negates any beneficial effect [Effect of blood on the efficacy of barrier adhesion reduction in the rabbit uterine horn model/C. B. Linsky, M. P Diamond., G. S. di Zerega et al.//Infertility.—1988.—Vol. 11.—P. 273-280].

Summing up the current approaches to the prevention of postoperative adhesions in the peritoneal cavity, Burlev V. A. et al. (2009) [Burlev V. A. Peritoneal adhesions: pathogenesis and prophylaxis. V. A. Burlev, E. D. Dubinskaya, A. S. Gasparov//Reproductive disorders.—2009.—No. 3.—P. 36-44] regret to state that all current methods for adhesion prevention are insufficiently effective (and quite expensive as well) and further studies are required to improve the efficacy of anti-adhesion measures.

The most similar to the present invention in technical terms is a method for the prevention of adhesions consisting in the injection of a combination of sterile Lintex-Mesogel gel and derinate into the serous sac [Method for the prevention of postoperative adhesions: Patent 2363476 of the Russian Federation: MKII51: A61K31/711, A61K31/717, A61P41/00/Gomon M. S., Lipatov V. A., Konoplya A. I., Bezhin A. I., Loktionov A. L., Kasyanova M. A., Sukovatykh B. S., Godova A. Yu.; patent applicant/holder Gomon M. S., Lipatov V. A.—No. 2007147670/14; submitted on Dec. 20, 2007; published on Aug. 10, 2009, Newsletter No. 22.—6 pages].

This method for the prevention of adhesions consists of the following procedure: During abdominal operation, for example, laparotomy or laparoscopy, and/or before the covering of the serous sac at the final stage of the surgical intervention, the areas with high probability of primary or recurrent adhesion development (for example, deseronized areas, anastomotic areas, areas with acute or possible inflammation, trauma zones after adhesion dissection, areas of abdominal drying, etc.) are treated with sterile Lintex-Mesogel gel and depot derinate. The volume of derinate is 1% to 25% of total mixture volume. The combination of the derinate and polymer gel is achieved when a mixture is prepared extemporaneously immediately before use, with the correct proportions of components. The ratio of gel-to-derinate solution volumes (based on 1.5 mg of derinate in 1 kg) should be such that the injected solution does not exceed 25% of the total volume, because more fluid may reduce the viscosity of the gel and its anti-adhesion activity. For adhesion prevention purposes, a portion of gel is applied to the serous surface using a syringe or squeezed into the palm of the surgeon's hand from the container where the mixture has been prepared and applied by smooth movements on the raw abdominal surface, deseronized areas and areas where adhesions may occur (areas with signs of inflammation or ischemia: edema, hyperemia, dilated vessels, discoloration, peristalsis, decreased pulsation of abdominal vessels, etc.). When diffusion processes occur (for example, after abdominal sanation in patients with generalized peritonitis), the combination of gel and derinate is applied at a dose calculated according to the table mentioned by G. DiZerega (1999 r.), that is 2.4 ml/kg for humans, and 10.7 ml/kg for animals (rats). When laparoscopic procedures are performed, specific injectors are used to apply gel with depot derinate.

Disadvantages of this method include the necessity to prepare the sterile solution during the operation, which can make the surgical process more complicated. Other disadvantages include difficulties in achieving homogeneity, difficulties in derinate dosing (need to be weighed), the need to use specific injectors/manipulators in laparoscopic procedures, and an absence of components inhibiting the activity of fibroblasts—cells which synthetic activity stimulates adhesion formation.

The p38 MAP-kinase inhibitor SB203580 is known to be an inhibitor of pro-inflammatory cytokine production [Badger A. M., Bradbeer J. N., Votta B. et al.

Pharmacological profile of SB 203580, a selective inhibitor of cytokine suppressive binding protein/p38 kinase, in animal models of arthritis, bone resorption, endotoxin shock and immune function//J. Pharmacol. Exp. Ther.—1996.—Vol. 279.—P. 1453-1461].

However, no data were obtained by the inventors and no literature references were found concerning the use of p38 MAP-kinase inhibitor as an agent exhibiting anti-adhesion activity.

SUMMARY OF THE INVENTION

The purpose of the subject matter of the present application is to develop compounds for the prevention and treatment of adhesions, and to develop pharmaceutical compositions containing a sufficient amount of one and/or several of the compounds described above and a pharmaceutically acceptable carrier, diluent or excipient.

Another purpose is to develop a method for adhesion prevention in order to avoid additional administration of medications in the postoperative period.

The inventors found out that p38 MAP-kinase inhibitors may be used for the treatment and prevention of adhesion formation. In particular, a compound [4-(4-fluorophenyl)-2-(4-methylsulfinylphenyl)-5-(4-pyridyl)-1H-imidazole], also known as SB203580 (chemical formula is shown in A. Cuenda et. al, FEBS Letters 364(1995) 229-233), and other new compounds of type (I)-(VII) (described below), prepared according to the present invention at the concentration of 0.1 to 100 μg/ml (on the basis of active substance inhibiting p38 MAP-kinase activity) and in the amount of 0.1 to 500 ml (depending on serous sac surface), are sufficient to moisten the serous sac surface and provide a barrier to adhesion formation in the injured serous sac, as seen in FIG. 1.

The subject matter of the present application is characterized by the development of new compounds for the prevention and treatment of adhesions showing an inhibiting activity targeted at excessive proliferation response when involved in pathological processes of serous surfaces, and by the development of pharmaceutical compositions containing a sufficient amount of one and/or several compounds for adhesion prevention, together with a method for the prevention and treatment of adhesions using these compounds.

The group of the compounds described above may be characterized by the following structural formulas.

Type (I):

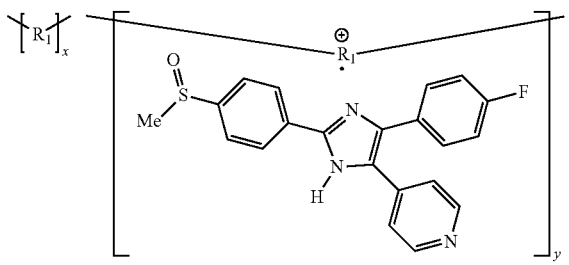

or type (II):

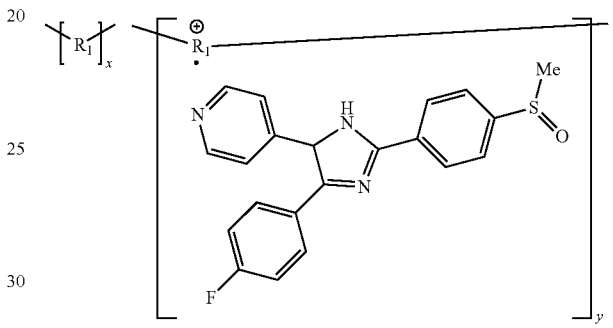

or type (III):

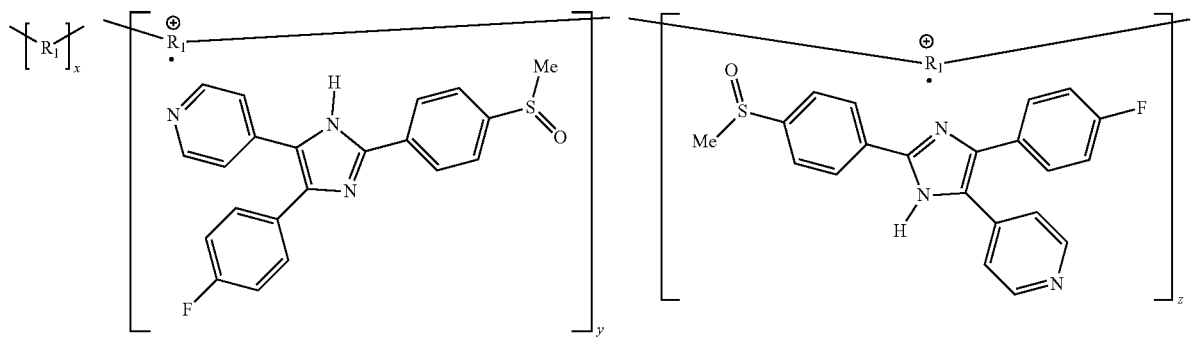

or type (IV):

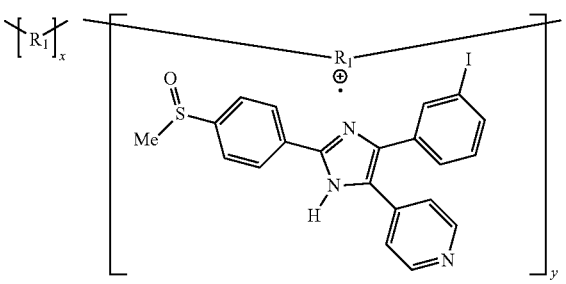

or type (V):

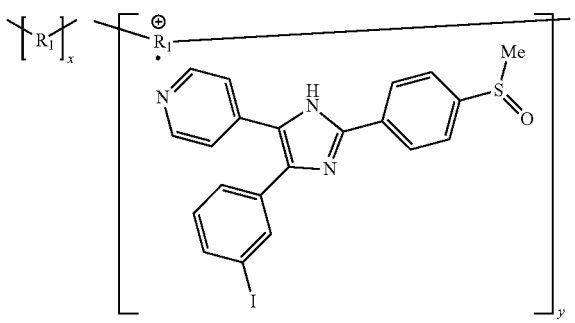

or type (VI):

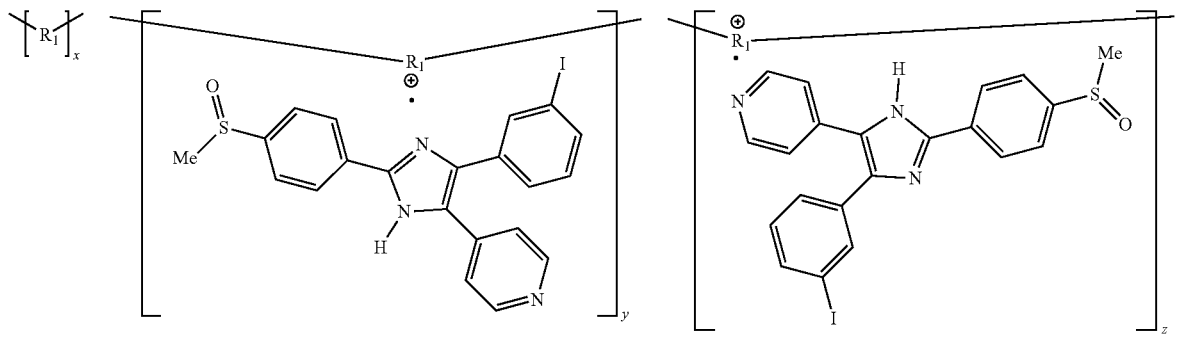

or type (VII):

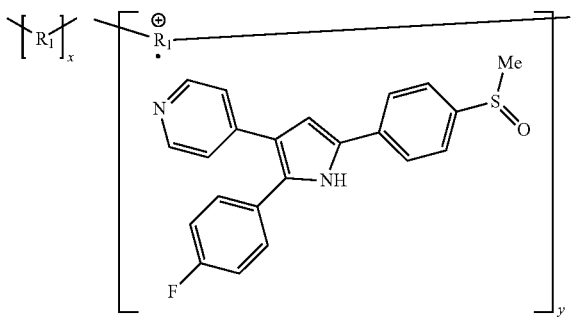

where $R_1$ is a base unit of water soluble polymers of natural or synthetic origin; x, y and z—integral values, where x, y and z≠0. X, Y and Z values depend on the number of monomer units in a polymer molecule. In fact, each molecule has n of monomers. Some of these monomers bind to the p38 MAP-kinase inhibitor, the rest of the molecule remains unbound. Thus, (X+Y)=n (or in some cases X+Y+Z=n), where n may be any integral number. In one embodiment of the present invention, x+y+z>10.

The subject matter of the present application relates to the use of SB203580 for new indications, namely as a compound exhibiting anti-adhesion activity.

Moreover, the subject matter of the present application relates to pharmaceutical compositions that are characterized by a sufficient amount of any of the described compounds of type (I)-(VII), or their combinations, or compound SB203580, or its combinations with any of the compounds of type (I)-(VII), and a pharmaceutically acceptable carrier, diluent or excipient.

The amount of the active ingredient in the pharmaceutical composition, namely the amount of the compound of type (I)-(VII) or compound SB203580 or their combinations, sufficient to achieve therapeutic effects, may vary depending both on the compound used or the route of its administration, and on the area of serous sac surface in a treated patient.

The acceptable dose of the compound of type (I)-(VII) or compound SB203580 used for the treatment of serous sac surface is about 0.01 µg to 50 mg on the basis of a compound inhibiting p38 MAP-kinase activity.

Although the active ingredient may be administered separately as a raw chemical substance, it is preferable to include it into the pharmaceutical composition. The amount of the active ingredient is also preferable to be 0.00001% to 99.99999% of the total pharmaceutical composition volume.

Therefore, drug formulations may be presented in the form of standard dosage units or single doses and may be prepared using any of the known pharmaceutical methods. Methods described in A. I. Tikhonov, T. G. Yarnykh "Medication Technology", published by NPU 2002, pages 228, 229, 242, may be used as one of the alternatives to prepare the pharmaceutical composition. All methods include the phase of interaction the active ingredient to the carrier, which consists of one or more excipients. Pharmaceutical compositions are usually prepared by the steady and close contact (of the active ingredient with the liquid carrier.

The pharmaceutical composition according to the subject matter of the present application can be prepared and administered in liquid form for perfusion systems, in the form of spray, spraying and vaporization solution, foamy aerosol, gel or suspension, or in any other liquid form.

In regard to the route of administration, it is appropriate to apply the solution over the serous sac surface, including wounds and organs, or to spray the solution for the prevention of adhesions using a special sprayer immediately after its preparation.

Once prepared, the adhesion prevention solution can be sprayed over the necessary areas, and the solution used for adhesion prevention in the wound areas also can be sprayed evenly over the necessary areas. The areas of potential adhesion formation can also be thoroughly sprayed.

For spraying the solution, a sprayer with two pressure pulverizers can be used, in which drops of the solution are transferred by air or carbon dioxide, or a sprayer with one pressure pulverizer, in which the solution turns into small particles.

The technical result of the subject matter of the present application lies in the fact that the compounds of type (I)-(VII) are generated by conjugation of the base polymer and a protonated derivate of pyridine-imidazole or pyridine-pyrrole, and that the pharmaceutical composition containing a sufficient amount of the compound of type (I)-(VII) and/or compound SB203580, and a pharmaceutically acceptable carrier, diluent or excipient has been prepared.

Any appropriate base polymer can be used to generate compounds of type (I)-(VII). It is preferable to use as base polymers polyethylenimine and its copolymers, polyvinylpyridines and their copolymers, polyvinylimidazole and its copolymers, polyvinyltriazole and its copolymers, chitosan and its derivates, carboxymethyl cellulose salts, polyacrylic acid and its copolymers, polymethacrylic acid and its copolymers, or polymethylmethacrylic acid and its copolymers.

In some embodiments, the subject matter of the present application also requires that the pharmaceutical composition is administered intraperitoneally during surgical, minimally invasive or diagnostic procedures for the prevention or treatment of any disease or medical condition associated with adhesion formation and/or development.

The method for prevention of adhesions consists in the following: An appropriate p38 MAP-kinase inhibitor is injected into the serous sac immediately after operative and/or diagnostic procedures.

As one of the variants for adhesion prevention, p38 MAP-kinase inhibitors, in particular SB203580 or one of the compounds of type (I)-(VII) or their combinations are injected in the sterile solution form at the concentration of 0.1 to 100 µg/ml (on the basis of active substance inhibiting p38 MAP-kinase activity) and in the sufficient amount to moisten the serous sac surface. The solution is administered once at a dose that may inhibit not less than 50% of p38 MAP-kinase activity in injured areas.

A specific feature of the method is that with a disease or medical condition associated with serous sac disorders the pharmaceutical composition containing SB203580 or one of the compounds of type (I)-(VII) or their combination is administered by the surgical subject.

The method can be used for the treatment of diseases or medical conditions accompanied by exudation or bleeding in the serous sac, or by damage to the serous membrane.

Compounds intended for adhesion prevention, pharmaceutical compositions containing these compounds and the method for the prevention and treatment of adhesions described in the present invention may be used in the fields of experimental and clinical medicine, and/or veterinary practice. Its functionality has been confirmed by the distinctive characteristics and features described above.

Thus, the inventors have demonstrated convincing evidence that p38 MAP-kinase inhibitors may be used as medications with anti-adhesion activity.

Moreover, the inventors have achieved the aim of generating compounds that are effective in the treatment and/or prevention of adhesions, and developed pharmaceutical compositions using these compounds with a sufficient amount of one of the compounds and/or their combination and a pharmaceutically acceptable carrier, diluent or excipient. Moreover, the inventors have developed an effective method for adhesion prevention allowing to avoid additional administration of medications in the postoperative period.

BRIEF DESCRIPTION OF DRAWINGS

For a fuller understanding of the invention, reference should be made to the following detailed description, taken in connection with the accompanying drawings, in which.

DETAILED DESCRIPTION

Figure 1:
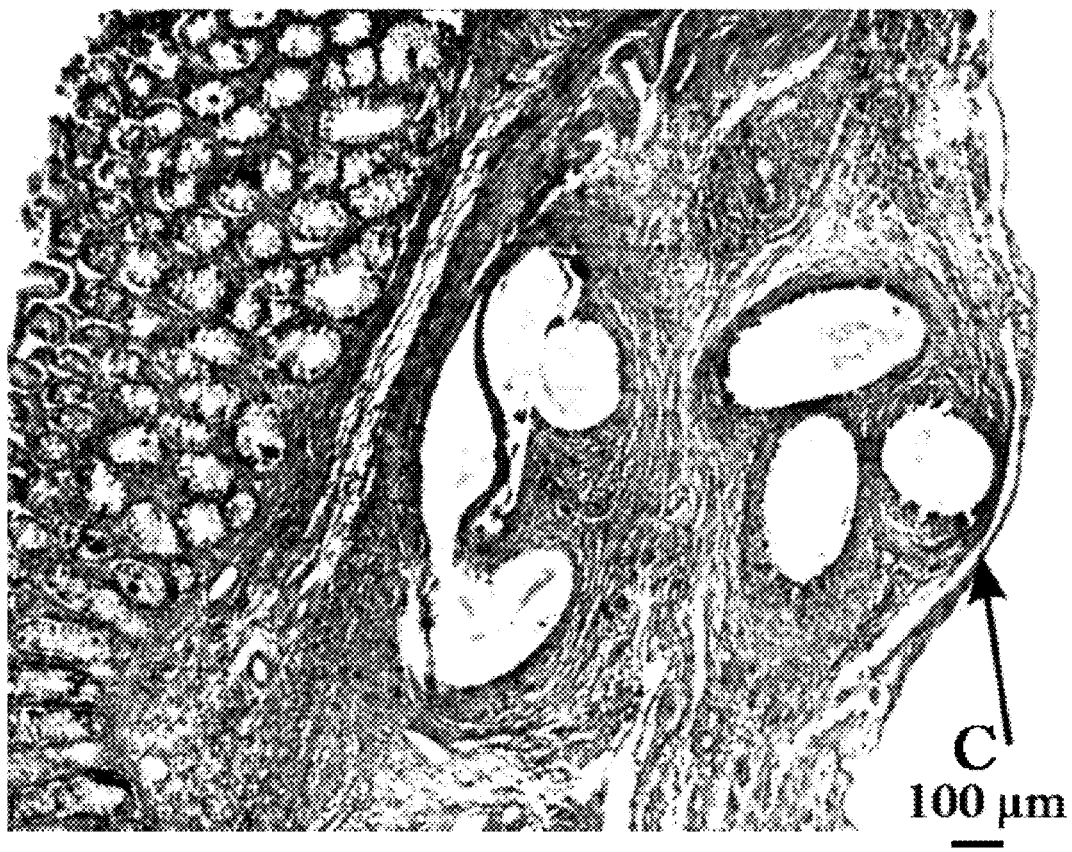
FIG. 1 shows the therapeutic efficacy of SB203580 through a histological section of the intestinal wall in the area of adhesion formation. No signs of adhesions are shown in the animal from the experimental group, even at the abdominal trauma zone and in the area of the postoperative suture (position C), van Gieson's staining.

The following examples are used as illustration, but not to limit the scope of the present invention.

Example 1

Preparation of the Compounds of Type (I)-(VII) with Anti-Adhesion Activity

Compounds of type (I)-(VII) were prepared during the three-phase process according to schemes 1-3 given below.

During the first phase, an aqueous-based polymer solution, for example, polyvinylimidazole, was prepared according to scheme 1 for the synthesis of the compounds of type (I)-(VII) with anti-adhesion activity.

During the second phase, aqueous protonated solutions of the compounds of type (I)-(VII) were prepared by dissolving them in the aqueous solution of any nonorganic or organic acid (HAn) according to scheme 2. Compound identity was confirmed using UV-VIS spectra for the aqueous solutions of the compounds of type (I)-(VII).

During the third phase, the obtained aqueous polymer solution was mixed with the aqueous solution of the compounds of type (I)-(VII), and incubated for 1 hour at room temperature until the complete degradation of protonated salts (degradation of salts exposed to the high-alkaline medium of aqueous polymer solutions) formed the compound of type (I)-(VII) as a conjugate of the base polymer and active ingredient (scheme 3).

UV-VIS spectra were recorded again and, according to their transformation (compared to protonated salts), the conjugation of compound of type (I)-(VII) with polymers was determined.

These compounds of type (I)-(VII), as opposed to parent compounds without polymers, may be used for the treatment and prevention of adhesion formation.

Scheme 1.

Preparation of Aqueous Polymer Solution

The selected polymer was suspended in water and permitted to protonate, as seen by the general equation:

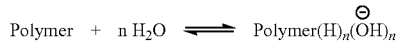

Preparation of Aqueous Polyvinylimidazole Solution

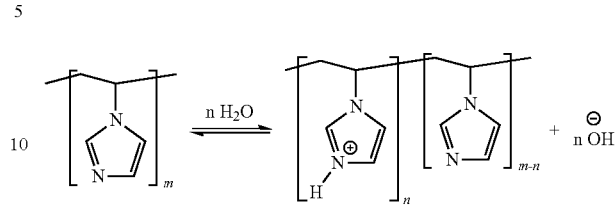

Preparation of Aqueous Carboxymethyl Cellulose Solution

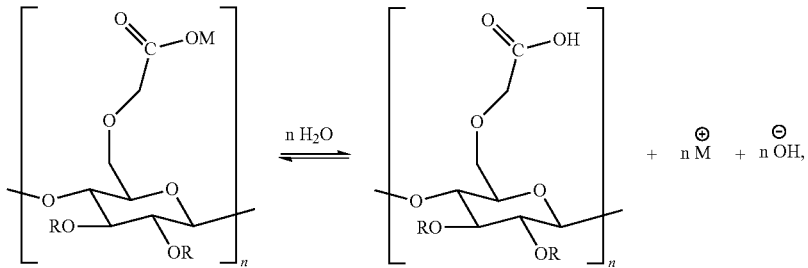

where R=H, $CH_2C(O)OM$; and M=$Na^+$, $K^+$, $NH_4^+$ etc.

Preparation of Aqueous Chitosan Solution

Scheme 2

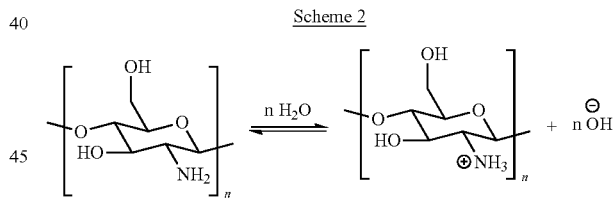

Preparation of Water-Soluble Protonated Compounds of Type (I)-(VII)

Scheme 3

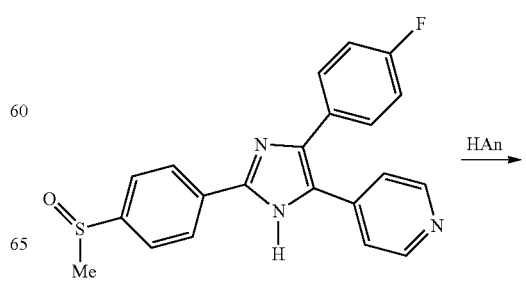

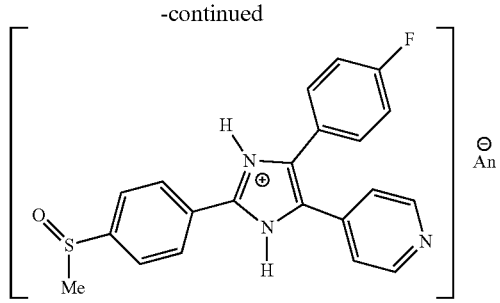

Preparation of the Compounds of Type (I)-(VII)

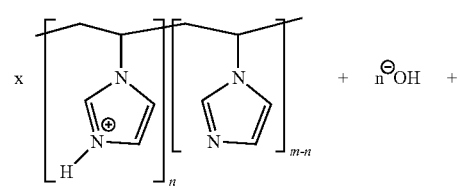

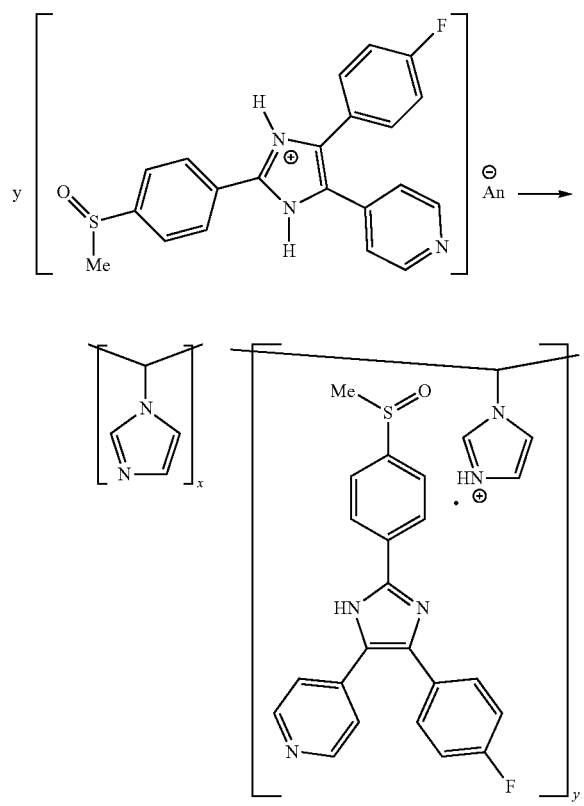

Example 2

According to schemes 1-3 given in example 1 (see above), a compound of type (I) was generated on the basis of chitosan, a polymer of natural origin:

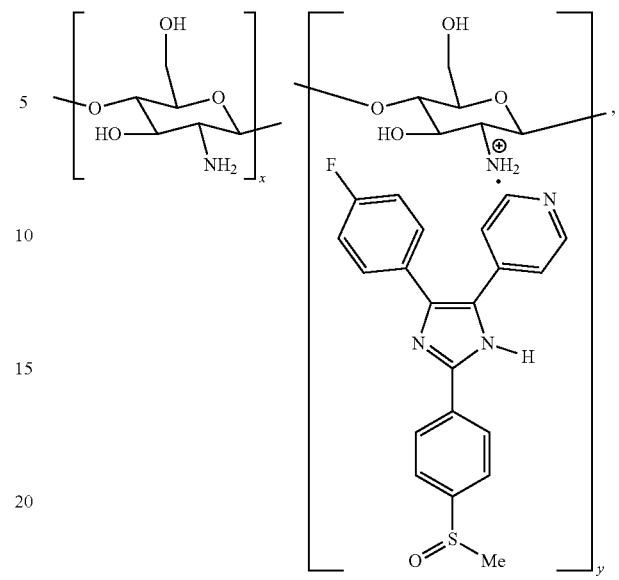

where x and y—integral values, x, y 0.

Example 3

According to schemes 1-3 given in example 1 (see above), a compound of type (I) was generated on the basis of polyvinylimidazole, a polymer of synthetic origin:

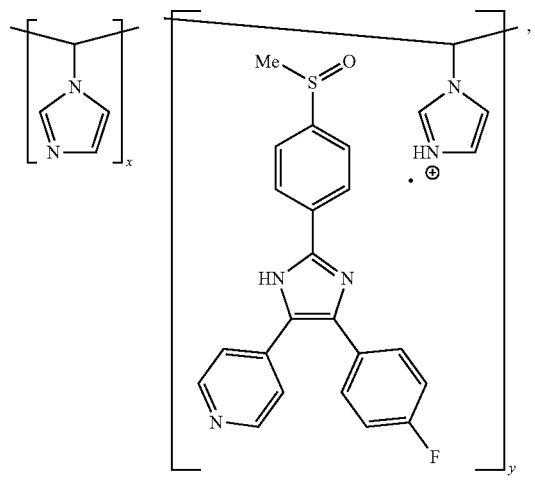

where x and y—integral values, x, y 0.

Example 4

According to schemes 1-3 given in example 1 (see above), a compound of type (I) was generated on the basis of carboxymethyl cellulose, a polymer of synthetic origin:

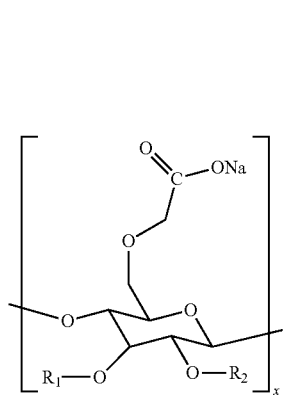 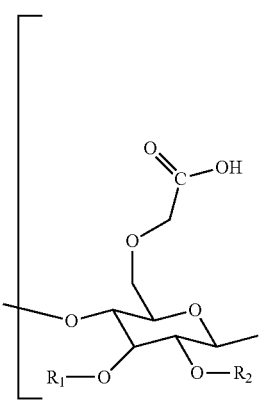 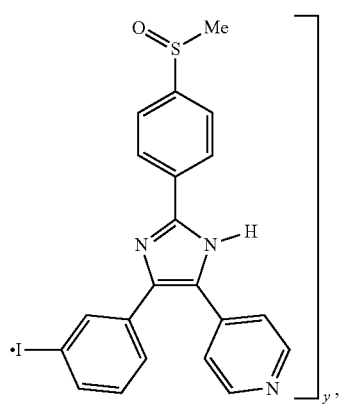

where x and y—integral values, x, y 0.

Example 5

Adhesions in the peritoneal cavity were generated in laboratory animals (Wistar rats, 9 months of age, weight of 220-250 g) by injuring the surface of caecum and abdominal wall scarification in the injured area. The study was conducted in compliance with the principles of the European Convention for the Protection of Vertebrate Animals used for Experimental and other Scientific Purposes (Strasbourg, France, 1986), as well as with regulations for humane treatment specified in Guidance for Proper Conduct of Animal Experiments (Attachment to Order No. 755 of the Ministry of Health of the USSR, dated Aug. 12, 1977).

Ten laboratory animals were used in this study. They were divided into 2 groups: the experimental group and the control group.

Before celiorrhaphy, 3 ml of sterile solution SB203580, p38 MAP-kinase inhibitor, at a concentration 10 µg/ml was injected once into the experimental animals. The calculation was based on the minimum volume of solution required to moisten the peritoneal surface (diZerega G. S. Peritoneum, peritoneal healing and adhesion formation/G. S. diZerega// in: Perotoneal surgery: Ed. G. S. diZerega.—Berlin—Heidelberg—New York: Springer, 2006.—P. 3-38), and the concentration was calculated on the basis of $IC_{50}$ in the boundary layer of cells. The control animals received a corresponding amount of normal saline solution.

On Day 28 after the abdominal cavity being injured, all animals were autopsied for the examination of abdominal cavity organs and the assessment of the severity and incidence of adhesions, deformation of abdominal cavity organs and distribution of different types of adhesions. The severity of adhesions was scored according to micro- and macroscopic adhesion scales [Micronized purified flavonoid fraction may prevent formation of intraperitoneal adhesions in rats//H. G. Yilmaz, I. H. Tacyildiz, C. Keles et al.//Fertil. Steril.—2005.—Vol. 84, Suppl. 2.—P 1083-1087].

The visceral peritoneum and abdominal organs involved in adhesion formation were examined histologically after fixation in FineFIX solution (Milestone), paraffin filling, staining with hematoxylin-eosin and van Gieson's staining.

Figure 2:
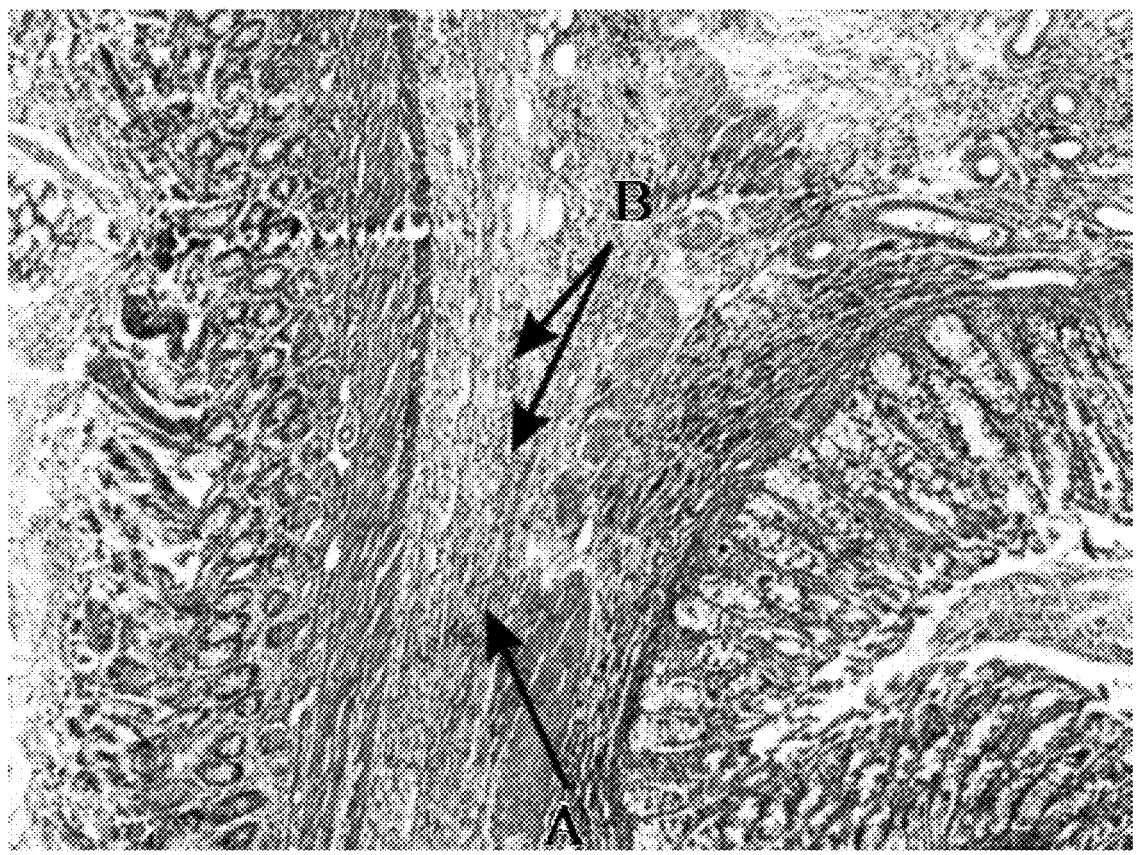
FIG. 2 shows the therapeutic efficacy of SB203580 through a histological section of the intestinal wall in the area of adhesion formation in an animal from the control group (van Gieson's staining). The observed adhesions are characterized by a greater length, density of connective tissue (position A), and signs of vascularization (position B).

Adhesions in the peritoneal cavity were observed in 100% of control animals. Control animals also exhibited intestinal wall adhesions in 100% of cases. FIG. 2 shows a histological section of the intestinal wall in the area of adhesion formation (position A) in the animal from the control group (van Gieson's staining). The observed adhesions were characterized by a greater length and density of connective tissue, and signs of vascularization (position B).

No cases of intestinal wall adhesions were observed in the experimental animals. FIG. 1 shows no signs of adhesions in the animal from the experimental group, even at the abdominal trauma zone and in the area of the postoperative suture (position C), van Gieson's staining.

The severity of adhesion formation was scored as 7 in the control group, as compared to a 2 in the experimental group ($p<0.01$).

Results of the study suggest that the described method may be used for the prevention of adhesions in the serous sac after surgical interventions.

Thus, the described method is considered to be efficient in preventing adhesion formation when the specified medication is injected once immediately after the operative procedures, and results in minimal injuries and simplifies the prevention of adhesions, while decreasing the risk of organ injuries and the risk of infections in the serous sac.

Example 6

Adhesions in the peritoneal cavity were generated in laboratory animals (Wistar rats, 9 months of age, weight of 220-250 g) by injuring the surface of the caecum and abdominal wall scarification in the injured area. The study was conducted in compliance with the principles of the European Convention for the Protection of Vertebrate Animals used for Experimental and other Scientific Purposes (Strasbourg, France, 1986), as well as with regulations for humane treatment specified in Guidance for Proper Conduct of Animal Experiments (Attachment to Order No. 755 of the Ministry of Health of the USSR, dated Aug. 12, 1977).

Thirty laboratory animals were used in this study. They were divided into 2 groups: the experimental group and the control group.

Before celiorrhaphy, a pharmaceutical composition (3 ml) containing the compound according to example 2, at a concentration of $2 \times 10^{-3}$ mol/l was injected once in experimental animals. The calculation was based on the minimum volume of solution required to moisten the peritoneal surface [diZerega G. S. Peritoneum, peritoneal healing and adhesion formation/G. S. diZerega//in: Perotoneal surgery: Ed. G. S. diZerega.—Berlin—Heidelberg—New York: Springer, 2006.—P. 3-38]). The control animals were injected with a corresponding amount of saline solution.

On Day 7, 14 and 28 after the abdominal cavity being injured, all animals were autopsied for the examination of abdominal cavity organs and the assessment of the severity and incidence of adhesions, deformation of abdominal cavity organs and distribution of different types of adhesions. The visceral peritoneum and abdominal organs involved in adhesion formation were examined histologically after fixation in FineFIX solution (Milestone), paraffin filling, staining with hematoxylin-eosin and van Gieson's staining.

Figure 3:
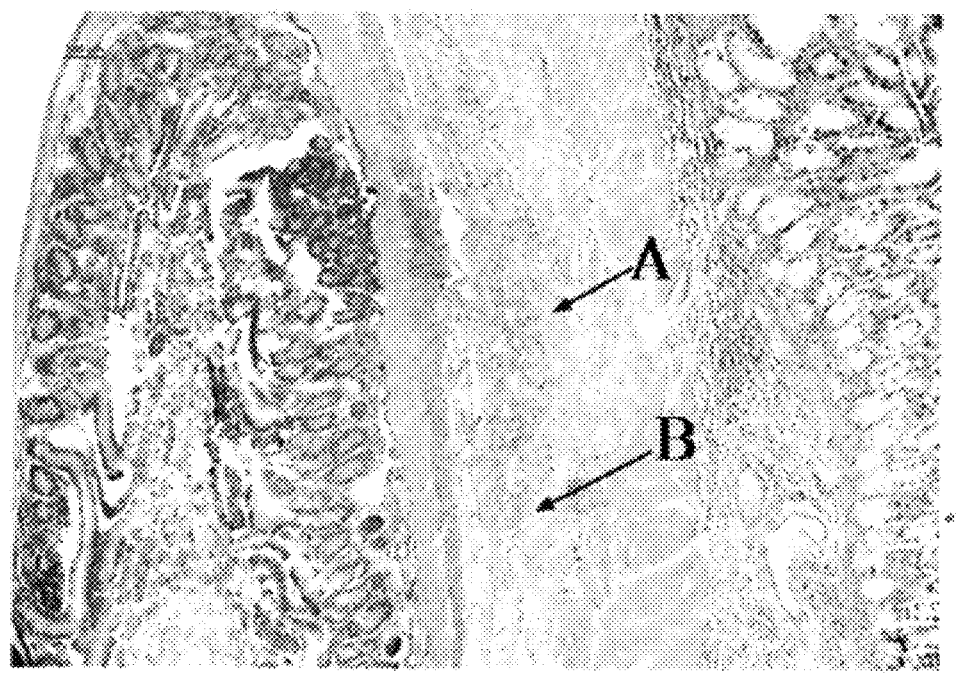
FIG. 3 shows the therapeutic efficacy of compound type I with polyvinylimidazole polymer through a histological section of the intestinal wall in the area of adhesion formation (position A) in an animal from the control group 30 days after modelling (van Gieson's staining). Intestinal wall adhesions (position A) and well-vascularized adhesions (position B) are shown.

Adhesions in the peritoneal cavity were observed in 100% of the control animals Intestinal wall adhesions were also detected in 100% of the controls. The observed adhesions were characterized by a greater length and density of connective tissue, and signs of vascularization, as seen in FIG. 3. Also, FIG. 3 shows a histological section of the intestinal wall in the area of adhesion formation (position A) in the animal from the control group 30 days after modelling (van Gieson's staining). Intestinal wall adhesions (position A) and well-vascularized adhesions (position B) were shown.

Figure 4:
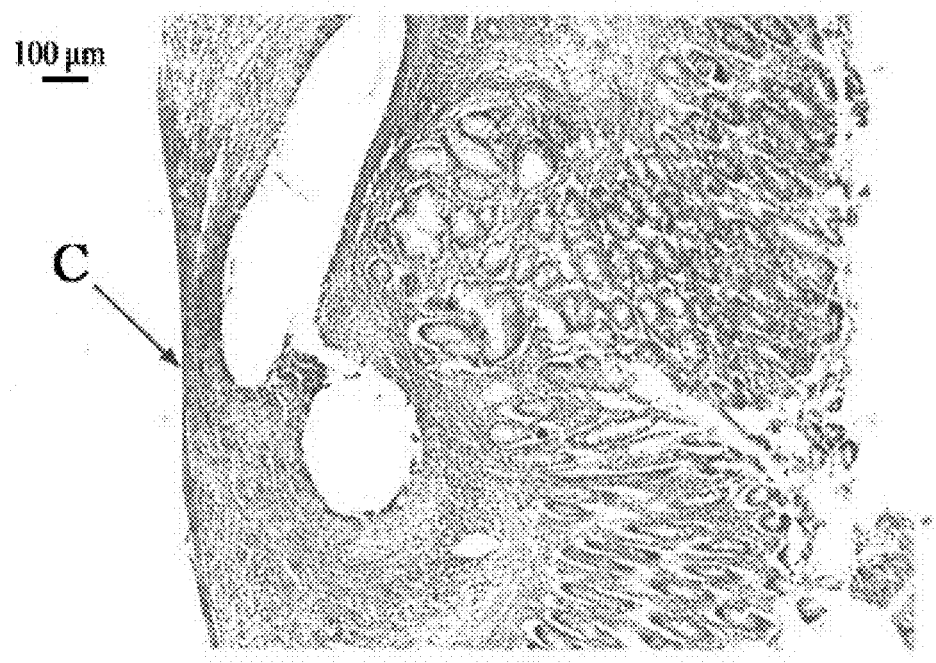
FIG. 4 shows the therapeutic efficacy of compound type I with polyvinylimidazole polymer through a histological section of the intestinal wall in the area of adhesion formation. No signs of adhesions in the animal from the experimental group are evident, even at the abdominal trauma zone and in the area of the postoperative suture (position C), 30 days after modelling (van Gieson's staining).

No cases of intestinal wall adhesions were observed in experimental animals. FIG. 4 shows no signs of adhesions in the animal from the experimental group, even at the abdominal trauma zone and in the area of the postoperative suture (position C), 30 days after modelling (van Gieson's staining).

Figure 5:
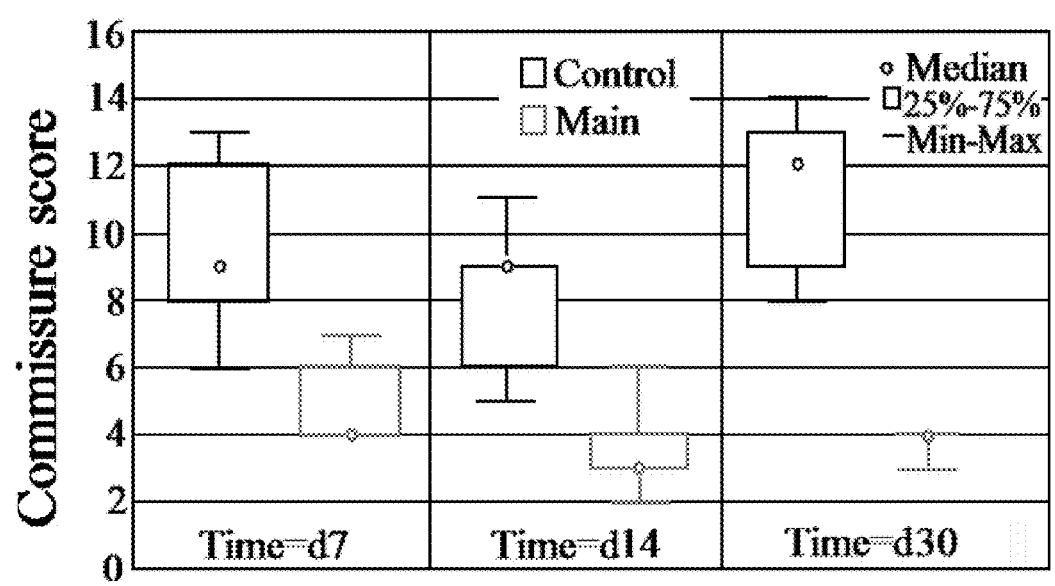
FIG. 5 shows the severity of adhesion formation on Day 7, 14 and 28 in the control group compared to that in the experimental group. The data shows the therapeutic efficacy of compound type I with polyvinylimidazole polymer.
Figure 6:
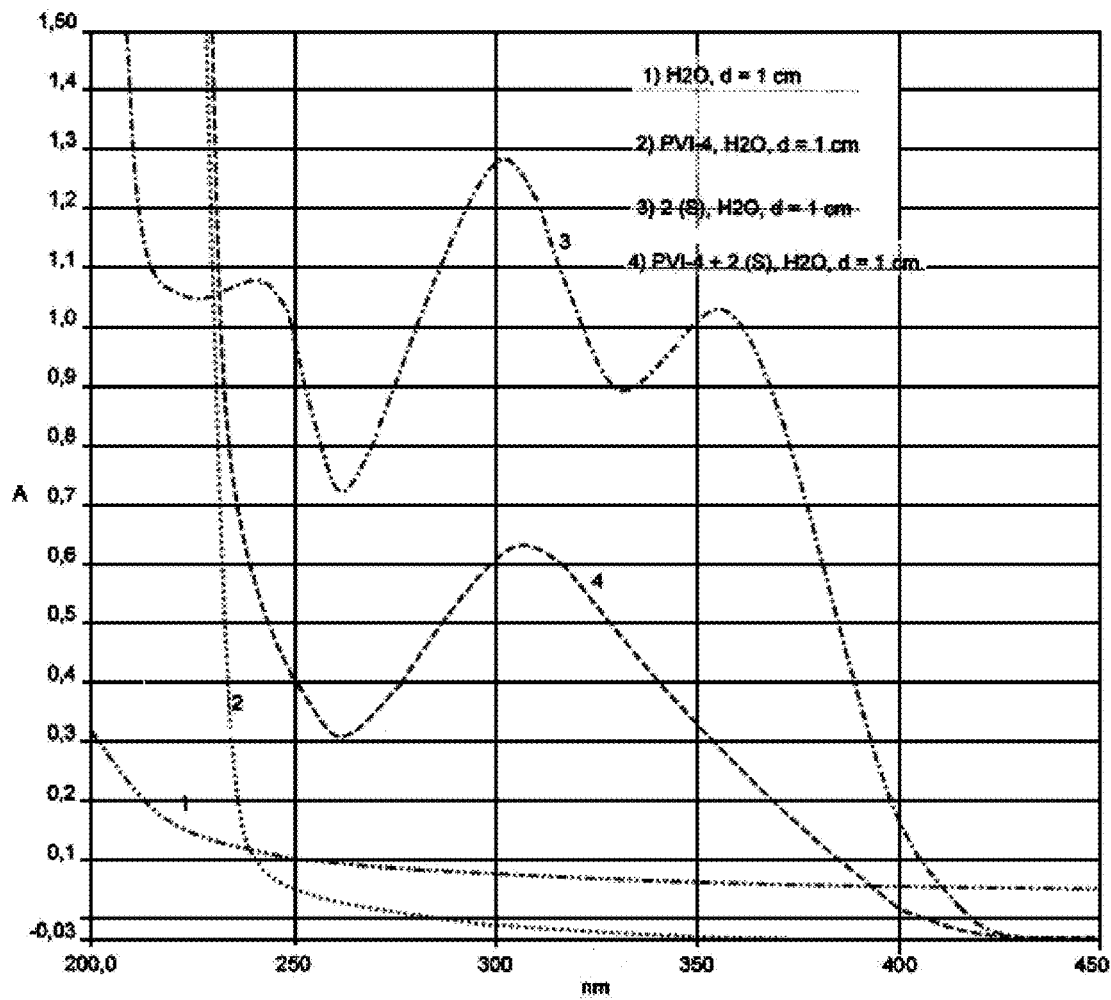
FIG. 6 UV-VIS spectrum of protonated salt aqueous solution of compound of type (I), where R1 is a base unit of polyvinylimidazole. Line 1—water, Line 2—aqueous solution of polyvinylimidazole, Line 3—compound (I), Line 4—compound (I)+polymer polyvinylimidazole.
Figure 7:
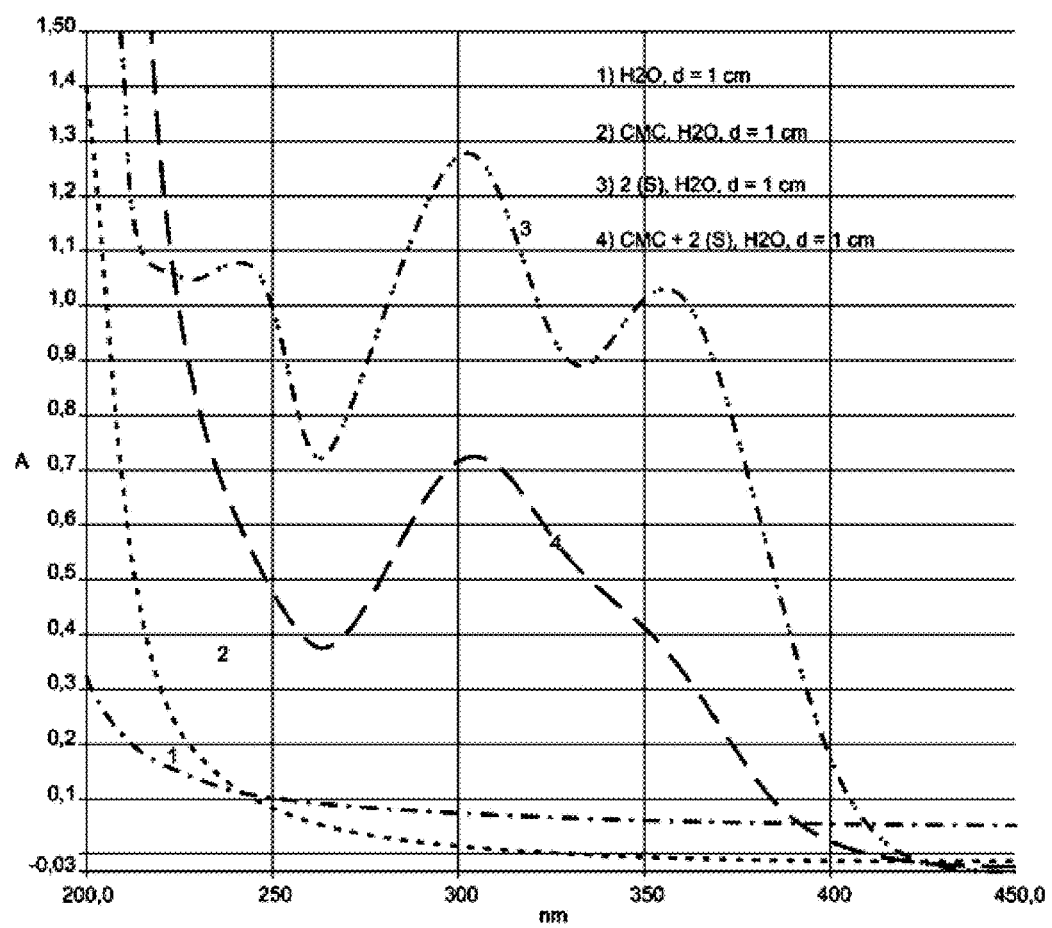
FIG. 7 UV-VIS spectrum of protonated salt aqueous solution of compound of type (I), where R1 is a base unit of carboxymethyl cellulose. Line 1—water, Line 2—aqueous solution of polyvinylimidazole, Line 3—compound (I), Line 4—compound (I)+polymer carboxymethyl cellulose.
Figure 8:
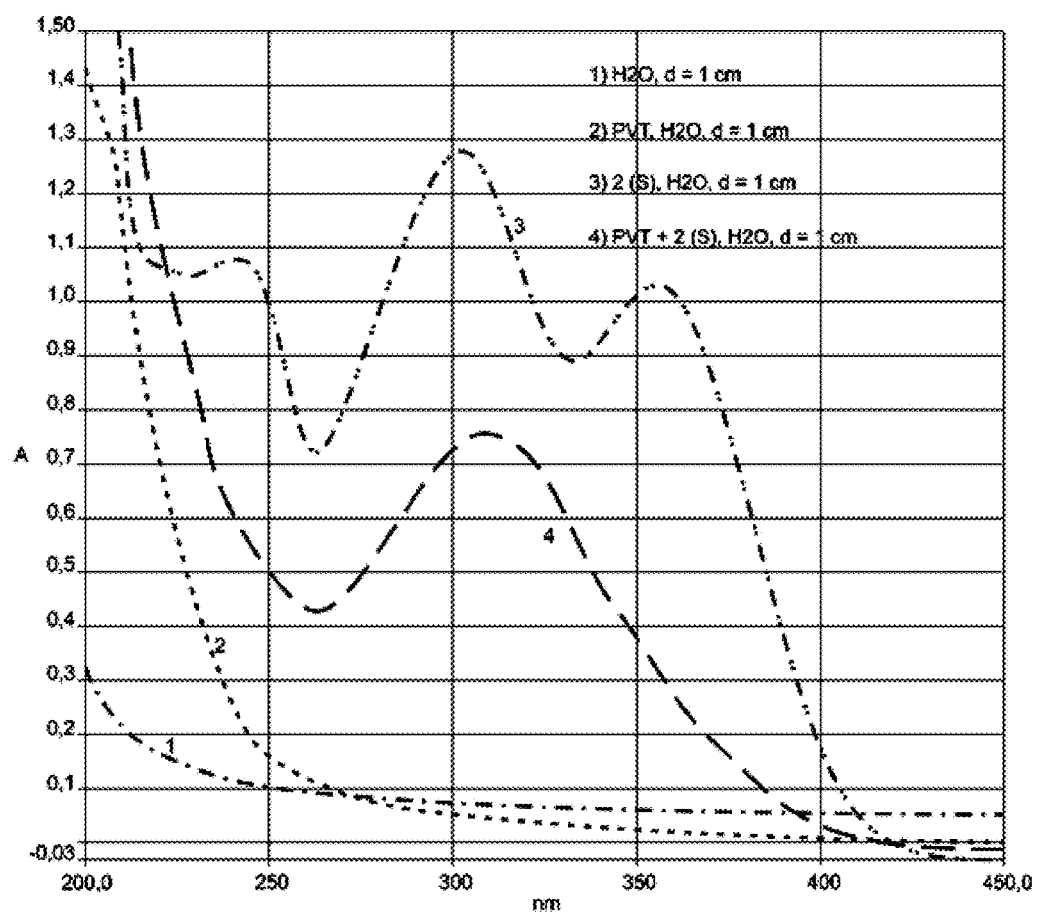
FIG. 8 UV-VIS spectrum of protonated salt aqueous solution of compound of type (I), where R1 is a base unit of polyvinyltriazole. Line 1—water, Line 2—aqueous solution of polyvinylimidazole, Line 3—compound (I), Line 4—compound (I)+polymer polyvinyltriazole.

On Day 7, 14 and 28, the severity of adhesion formation was significantly higher in the control group than in the experimental group, as seen in FIG. 5.

Example 7

Adhesions in the peritoneal cavity were generated in laboratory animals divided into 8 experimental groups, each composed of 25 individuals (Wistar male rats, 9 months of age, weight of 180-200 g) to evaluate the effects of the compounds of type (I)-(VII) on the basis of chitosan, carboxymethyl cellulose, polyvinyltetrazole, polyethylenimine, polyvinyltriazole, and polyacrylic acid on the prevention and course of adhesions. The study was conducted according to the methods described in example 5 and 6 of the present invention.

Compounds of type (I)-(VII) on the basis of chitosan, carboxymethyl cellulose, polyvinyltetrazole, polyethylenimine, polyvinyltriazole, and polyacrylic acid (at a dose of 10 mg/kg based on the compound inhibiting p38 MAP-kinase activity) were injected in the sterile solution form in animals of all experimental groups (once, after the surgical intervention) after the modeling of adhesion formation.

The control animals were injected with a corresponding amount of saline solution.

On 7, 14 and 28 day, following the peritoneal damage, animals underwentan autopsy, with a thorough study of abdominal organs for evaluation of significance and prevalence of commissural process, deformation of abdominal organs and structure of distribution of separate types of commissures. Visceral peritoneum and abdominal organs, involved in the commissural process, were histologically studied after fixation in solution FineFIX (Milestone), filling in paraffin, staining of sections involving hematoxilyn-eosin and by Van-Gieson method.

It was revealed that commissural process in abdominal cavity was registered in 100% cases and commissures of the intestinal wall were registered in 100% cases in animals of control group. By comparison, commissures of the intestinal wall were not registered in any of the animals in each of the six experimental groups. Expression of commissural process in animals of control group was consistently higher than in any of the experimental groups during follow up testing on 7, 14 and 30 days.

Example 8

Preparation of Conjugates of Polyvinylimidazole and 4-(4-Fluorinephenyl)-2-(4-Methylsulphinylphenyl)-5-(4-Pyridyl)-1H-Imidazole (Compound of Type (I))

A water solution of polyvinyl imidazole was prepared according to scheme 1 in Example 1. Then water solutions of protonated salt of type (I) compound were prepared by its dissolution in water solution of hydrochloric acid according to scheme 2 in Example 1. The UV-VIS spectra were acquired for the solution of protonated salt of type (I) compound.

According to scheme 3 in Example 1, the acquired water solution of polyvinylimidazole and water solution of protonated salt of type (I) compound were mixed, and held for 1 hour at room temperature for complete reverse decay of protonated salt of compound to form a water solution of conjugate of polyvinylimidazole and salt of 4-[4-(4-fluorinephenyl)-2-(4-methylsulphinylphenyl)-1H-imidazolyl-5-pyridine (hereafter "conjugate").

The UV-VIS spectra were tested again to confirm the compound's transformation (in comparison with protonated salt) formation of compound of type (I) with polyvinyl imidazole.

Example 9

Preparation of Conjugate of Polymethacrylate 4-(2-(4-fluorinephenyl)-5-(4-methylsulphinyl)phenyl)-1H-pyrrole-3-yl)pyridine (Compound of Type (II))

The conjugate is prepared according to schemes 1-3 in Example 1. Conjugate efficiency was 96%.

At room temperature, $^1$H NMR spectrum was obtained using a ECA 600 spectrometer with working frequency for nuclei $^1$H 600 MHz: (5% weight B H$_2$O-d$_2$, 25° C., JEOL ECA 600, ppm): 1.8-2.2 (2H, two signals CH$_2$ (I)), 2.4-2.8, 3.0-3.2 and 4.6-4.7 (1H, signals CH in syndiotactic, heterotactic and isotactic fragments I), 6.4-7.1 (3H, CH groups of imidazole cycle I), and also signals of far less intensity at 8.3, 8.0, 7.7, 7.5, 7.4, 7.3 (by 2H, CH groups of aromatic rings II), 2.7 (3H, singlet CH$_3$ of group II). The Bellied character of all signals does not allow to measure Spin-spin coupling constant, i.e. unambiguously refer signals of aromatic protons II.

Example 10

Preparation of Conjugate 4-(4-(4-fluorinephenyl)-2-(4-(methylsulphinyl)phenyl)-1H-imidazolyl)pyridine with Polyvinyl(1H-imidazole)4-(4-(4-fluorinephenyl)-2-(4-methylsulphinyl)phenyl)-1H-imidazolyl) pyridine (Compound of Type (III))

The conjugate was prepared according to schemes 1-3 in Example 1. Conjugate efficiency was 97%.

At room temperature $^1$H NMR spectrum was registered on ECA spectrometer with working frequency for nuclei $^1$H 600 MHz: (5% weight B H$_2$O-d$_2$, 25° C., JEOL ECA 600, ppm): 1.50 p (CH$_3$); 2.20 t (CH$_2$); 3.89 m (CH); 7.8 s (NH).

Example 11

Preparation of Conjugate of polyvinyltetrazole and 4-[5-(4-iodide-phenyl)-2-(4-methylsulphinylphenyl)-3H-imidazole-4-yl]-pyridine (Compound of Type (IV))

The conjugate was prepared according to schemes 1-3 in Example 1. Conjugate efficiency was 95%.

At room temperature IR spectrum in table KBr was registered on spectrometer Perkin-Elmer 1310, cm$^{-1}$: 3300 (N—H, C—H oscillations); 2200-1600 (peculiarities of oscillations C=C, C=N in N-heteroaromatic polymers); 1500-1400 (aromatic C=C oscillations); 1000-900 (=C—H, S=O).

Example 12

Preparation of Conjugate of Chitosan and 4-(5-(3-iodidephenyl)-2-(4-(methylsulphinyl)phenyl)-1H-pyrrolyl-4-yl)pyridine (Compound of Type (VII))

The conjugate was prepared according to schemes 1-3 in Example 1. Conjugate efficiency was 96%.

At room temperature $^1$H NMR spectrum was registered on JEOL ECA 600 spectrometer with working frequency for nuclei $^1$H 600 MHz: (5% weight B H$_2$O-d$_2$, 25° C., JEOL ECA 600, ppm): 1.8-2.2 (2H, two signals CH$_2$ (I)), 2.4-2.8, 3.0-3.2 and 4.6-4.7 (1H, signals CH in syndiotactic, heterotactic and isotactic fragments I), 6.4-7.1 (3H, CH groups of imidazole cycle I), and also signals of far less intensity at 8.3, 8.0, 7.7, 7.5, 7.4, 7.3 (by 2H, CH groups of aromatic rings II), 2.7 (3H, singlet of CH$_3$ group II). Bellied character of all signals does not allow to measure spin-spin coupling constant, i.e. unambiguously refer signals of aromatic protons II. There is an additional signal from 1H at C$_4$ in spectrum, but it cannot be revealed because it is covered under much more intensive signals of aromatic protons I.

Example 13

During the scientific studies of commissural formation process in abdomen it was discovered that intensity of commissural process correlates to activity of p38 MAPK in submesothelial layer of cells in 3-7 days after procedures on organs, covered with serous membrane. During artificial decrease of p38 MAPK activity in subserous tissues, commissural formation was found to either stop or significantly decrease, and the process of mesothelization, based on homing of mesotheliocytes in focuses of deserousing, does not undergo significant changes. These molecular biological studies, first in the world, evidence the effectiveness of the use of the present compounds for preventive care of commissural formation.

The phosphorylated (active) form of p38-phospho MAPK was examined using fibroblast cultures. 5 compound-groups were studied and in cultural medium of three groups at the beginning of cultivation one of the claimed substances was added once: Group 1 consisted of the composition of formula III, in which polyvinyltetrazole is used as a polymer, and values of x, y and z, based on the NMR study, were 18, 5 and 1, respectively. Group 2 consisted of the composition of formula VI, in which the sodium salt of carboxymethylcellulose was a polymer, and ratio of coefficients x, y, z was 16:7:2. Group 3 consisted of the composition of formula VII, in which chitosan was a polymer and x:y ratio was 8:1. In group 4 SB203580 was added in cultural medium, and in control group the medium was used without any additions.

Figure 9:
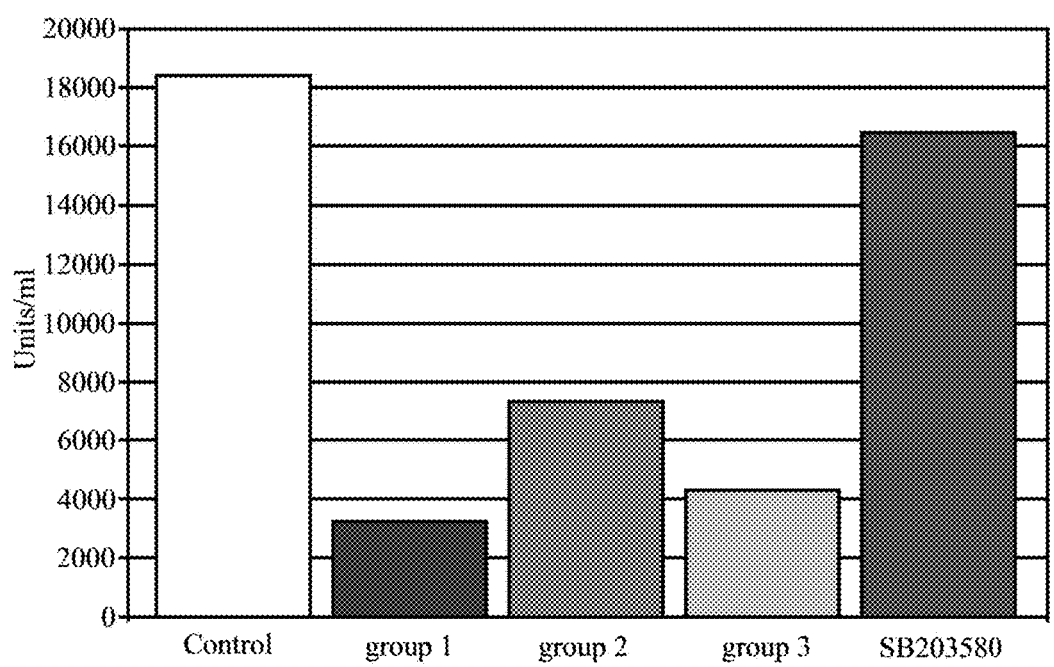
FIG. 9 is a graph showing p38-phospho MAPK in cell lysates 7 days of incubation after stimulation of FGF2.

Activity of p38-phospho MAPK was determined in lysates of cells after 7 days of incubation, using set Phospho p38 (T180/Y182) Flex Set (BD Bioscience) on running cytometer FACScalibur. The culture was stimulated by addition of mitogen—FGF2 prior to determination of content of phosphorylated form of p38 MAPK. The content of active form of p38-phospho MAPK was recorded, as seen in FIG. 9.

The high level of p38phospho activity in the SB203580 group was unexpected. However, introduction of SB203580 in combination with FGF2 led to an abrupt decrease of content of active form p38 MAPK to 1038±215 U/ml, which had a brief effect as seen by a return of active p38 MAPK 7 days after initial incubation. By comparison, the conjugates, i.e. compounds of types (I)-(VIII) conjugated with polymers, continued to demonstrate their activity.

Lung fibroblast cell cultures were prepared from Wistar rats using tissue homogenization. The cells were treated with enzymes for cell separation and inoculated into culture plates with nutritive medium supplemented with embryonic serum. After the initial inoculation, the cells were incubated in CO$_2$ incubator, and established colonies of fibroblasts were reseed for further studies. Commercially available p38 MAP kinase inhibitors, VX-702 and TAK-715 inhibitors, that were acquired from AbcamBiochemicals, and SB239063 inhibitor from Tocris Bioscience were added to nutritive medium during changing. The compounds of formulas (I)-(VII) conjugated with polyvinyltetrazole was added to cultures, in which p38 MAP kinase inhibitor, either alone as a conjugated compound, or in combination with the selective p38 inhibitors trans-4-[4-(4-fluorinephenyl)5-(2-methoxy-4-pyrimidinyl)-1H-imidazole-1-yl]cyclohexanol (SB239063); 6-(N-carbamoyl-2,6-difluorineanilino)-2-(2,4-difluorinephenyl)pyridine-3-carboxamide (VX-702); and/or N-[4-[2-ethyl-4-(3-methylphenyl)-1,3-thiazole-5-yl]-2-pyridyl]benzamide (TAK-715). It is noted that SB239063, VX-702, and TAK-715 have significantly different structure from the non-polymeric parts of the conjugates, i.e. the compounds shown in formulas (I)-(VII). During short incubation (6 hours) in the primary culture of the lung fibroblasts the p38 MAPK activity was analyzed.

Figure 10:
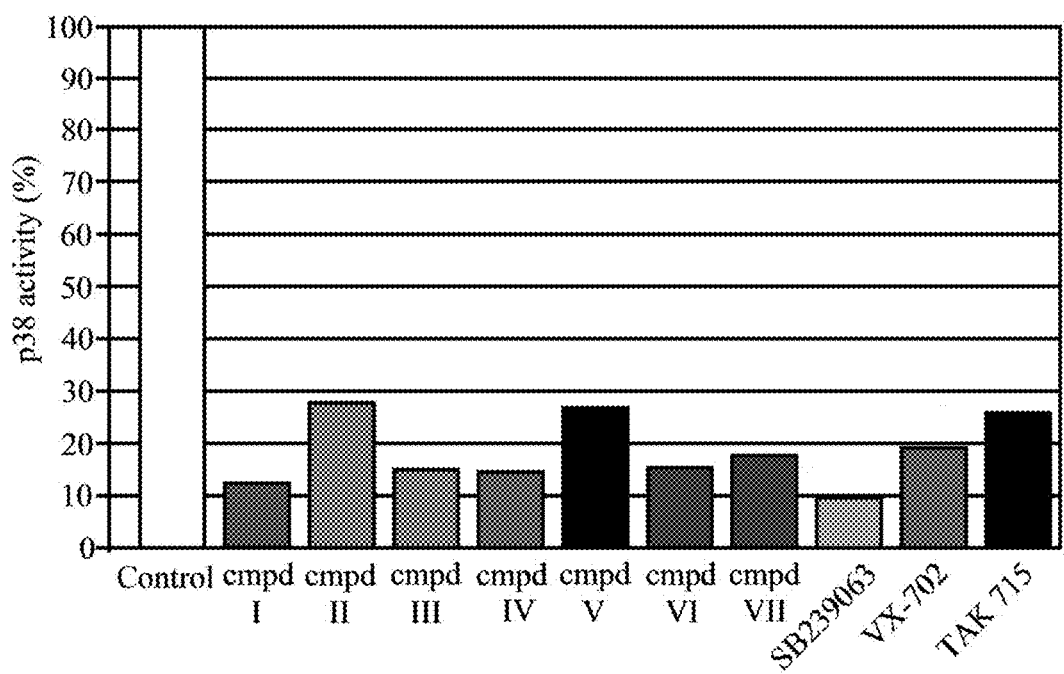
FIG. 10 is a graph showing activity of phosphor-p38 in tissue treated with various compounds of the invention compared to control (addition of placebo, designated as 100%).

The results evidence that all studied compounds have an inhibiting effect on p38 which are effective at preventing the formation of active form p38. Activity of p38 phospho in comparison with control (addition of placebo, designated as 100%) is presented in FIG. 10.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of adhesion treatment compositions, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating adhesion formation after surgery in a patient in need thereof comprising:

administering a therapeutically effective amount of a composition comprising a p38 MAP kinase inhibitor to the patient in need thereof, wherein the p38 MAP kinase inhibitor is a conjugated compound of a polymer base and protonated drug, having formula:

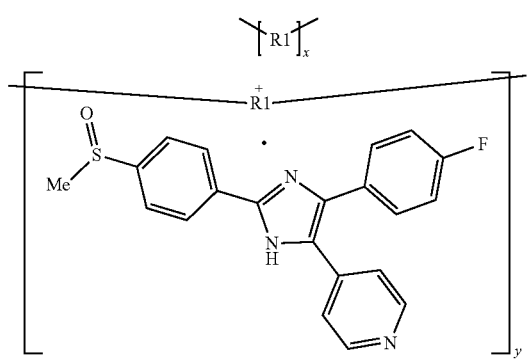

I

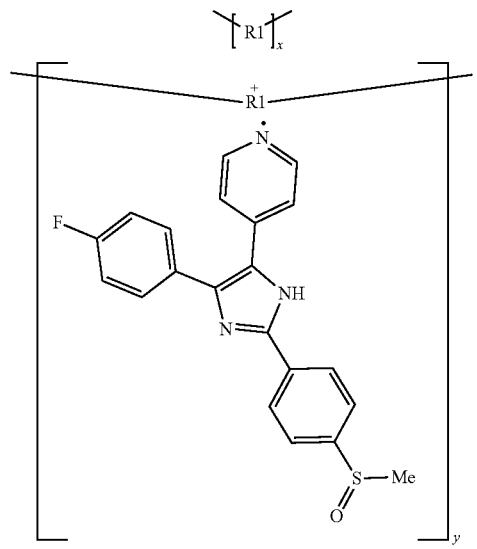

II

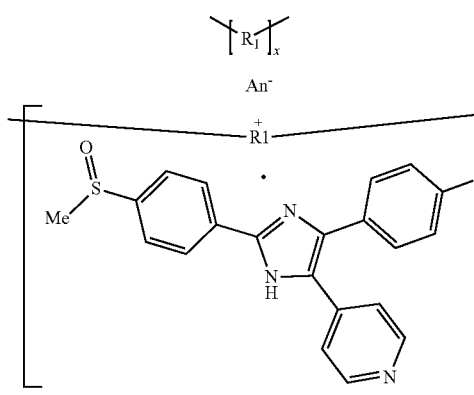

III

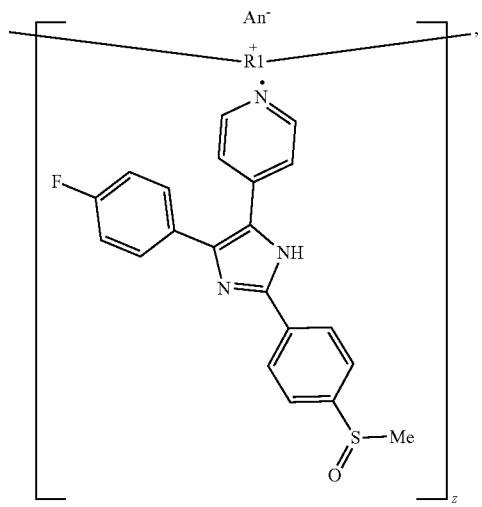

IV

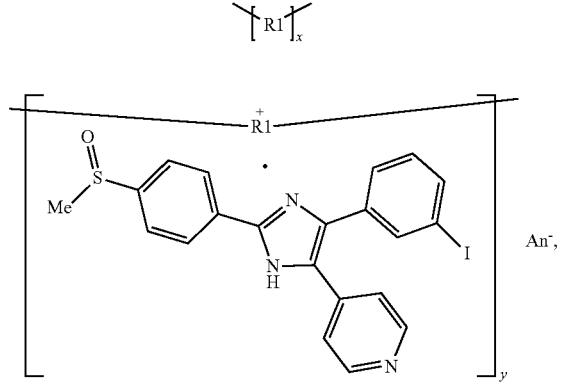

V

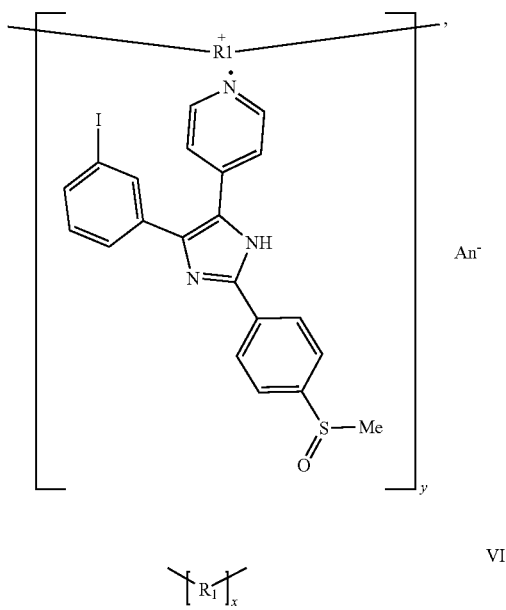

VI

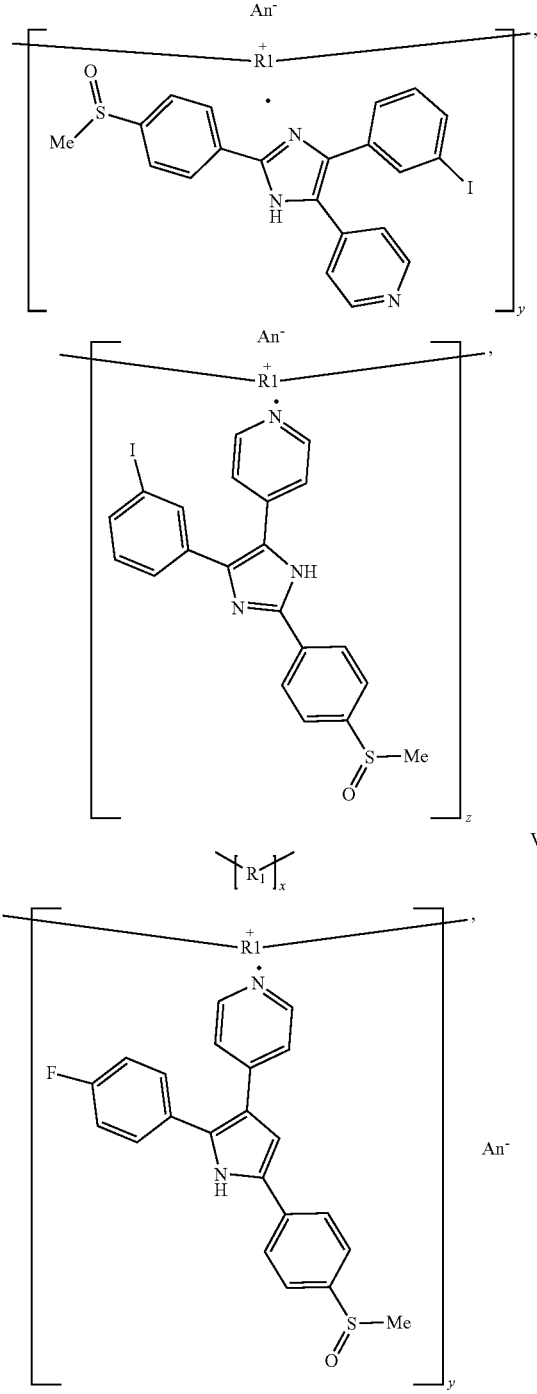

4-(4-fluorophenyl)-2-(4-methylsulfinylphenyl)-5-(4-pyridyl)-1H-imidazole, or a combination thereof;

wherein R1 is a protonated structural unit of a basic, water-soluble polymer;

wherein the basic, water-soluble polymer is polyethylenimine, a copolymer of polyethylenimine, polyvinylpyridine, a copolymer of polyvinylpyridine, polyvinylimidazole, a copolymer of polyvinylimidazole, polyvinyltriazole, a copolymer of polyvinyltriazole, chitosan, a derivative of chitosan, carboxymethyl cellulose salts, polyacrylic acid salts, a copolymer of polyacrylic acid salt, polymethacrylic acid, a copolymer of polymethacrylic acid, polymethylmethacrylic, or a copolymer of polymethylmethacrylic;

wherein the drug has a basic moiety that conjugates with the protonated structural unit of the water-soluble polymer; and wherein x, y and z are integers having a value of at least 1.

2. The method of claim 1, wherein the composition further comprises a pharmaceutically acceptable carrier, solvent or excipient.

3. The method of claim 1, wherein the basic, water-soluble polymer is of natural or synthetic origin.

4. The method of claim 1, wherein the basic, water-soluble polymer is chitosan.

5. The method of claim 1, wherein the composition is in liquid form.

6. The method of claim 5, wherein the composition is administered via injection into the patient after surgery.

7. The method of claim 6, wherein the composition is administered once.

8. A method of preventing adhesion formation in a patient in need thereof, comprising:

administering a therapeutically effective amount of a composition comprising a p38 MAP kinase inhibitor to the patient in need thereof, wherein the p38 MAP kinase inhibitor is a conjugated compound of a polymer base and protonated drug, having formula:

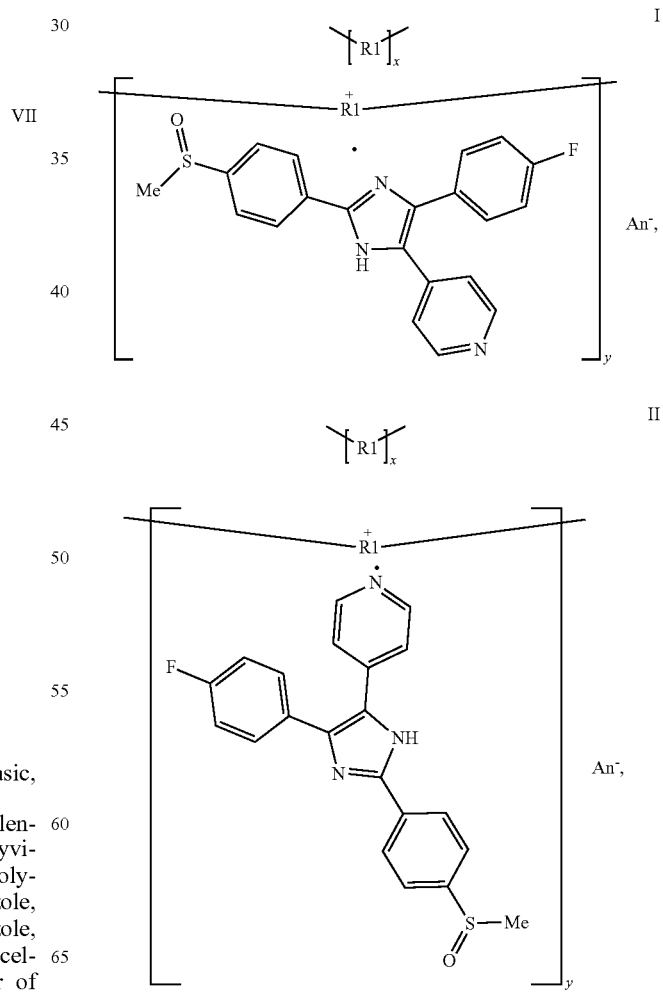

III
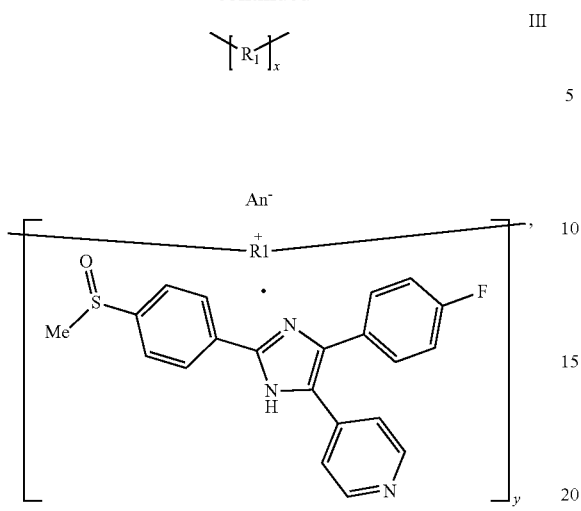
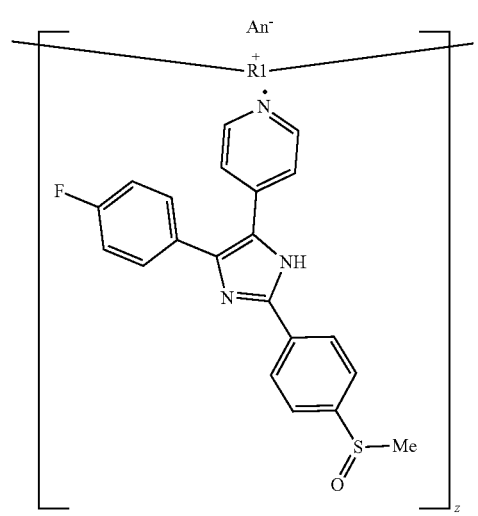
IV
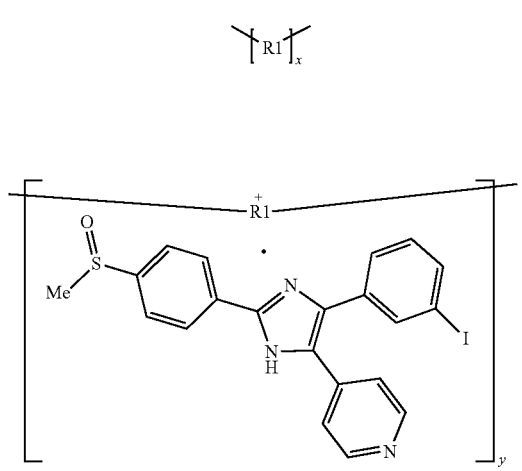
V
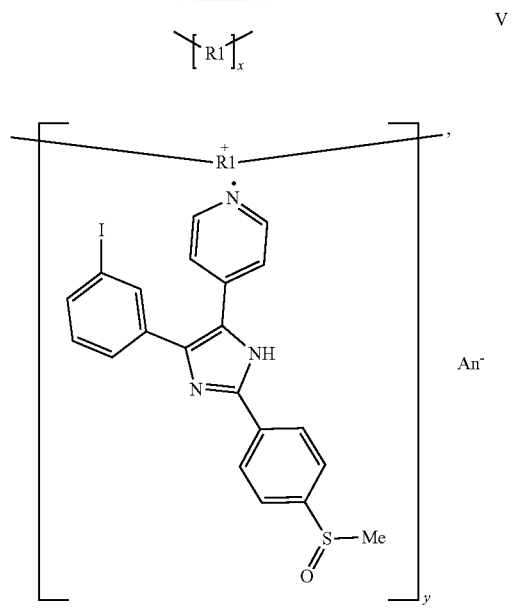
VI
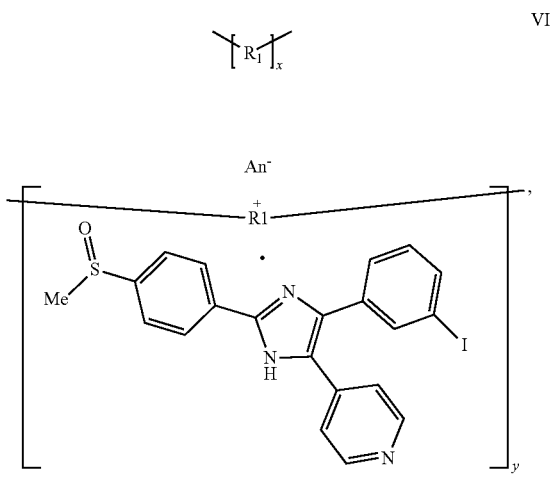
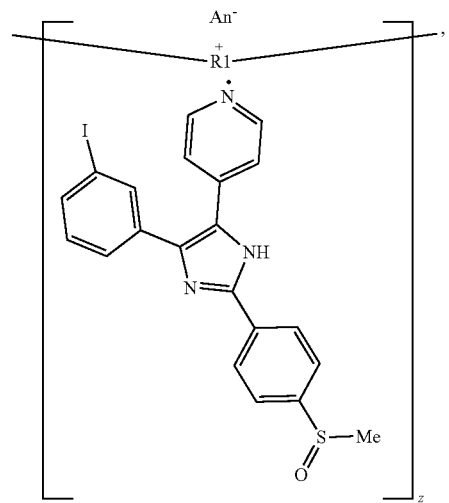

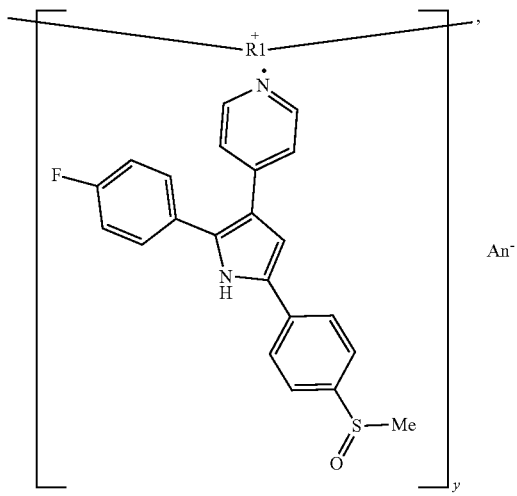

4-(4-fluorophenyl)-2-(4-methylsulfinylphenyl)-5-(4-pyridyl)-1H-imidazole, or a combination thereof;

wherein R1 is a protonated structural unit of a basic water-soluble polymer;

wherein the basic, water-soluble polymer is polyethylenimine, a copolymer of polyethylenimine, polyvinylpyridine, a copolymer of polyvinylpyridine, polyvinylimidazole, a copolymer of polyvinylimidazole, polyvinyltriazole, a copolymer of polyvinyltriazole, chitosan, a derivative of chitosan, carboxymethyl cellulose salts, polyacrylic acid salts, a copolymer of polyacrylic acid salt, polymethacrylic acid, a copolymer of polymethacrylic acid, polymethylmethacrylic, or a copolymer of polymethylmethacrylic;

wherein the drug has a basic moiety that conjugates with the protonated structural unit of the water-soluble polymer; and wherein x, y and z are integers having a value of at least 1.

9. The method of claim 8, wherein the composition further comprises a pharmaceutically acceptable carrier, solvent or excipient.

10. The method of claim 8, wherein the basic, water-soluble polymer is of natural or synthetic origin.

11. The method of claim 8, wherein the basic, water-soluble polymer is chitosan.

12. The method of claim 8, wherein the composition is administered after a surgical procedure and prior to celiorrhaphy.

13. The method of claim 8, wherein the composition is in liquid form.

14. The method of claim 13, wherein the composition is administered via injection into the patient.

15. The method of claim 14, wherein the composition is administered once to the patient.

16. A method of treating serous sac disorders associated with formation of adhesions in a patient in need thereof comprising:

administering a therapeutically effective amount of a composition comprising a p38 MAP kinase inhibitor to the patient in need thereof, wherein the p38 MAP kinase inhibitor is a conjugated compound of a polymer base and protonated drug, having formula:

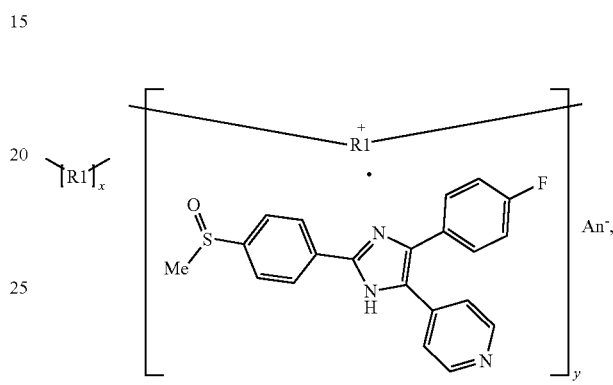

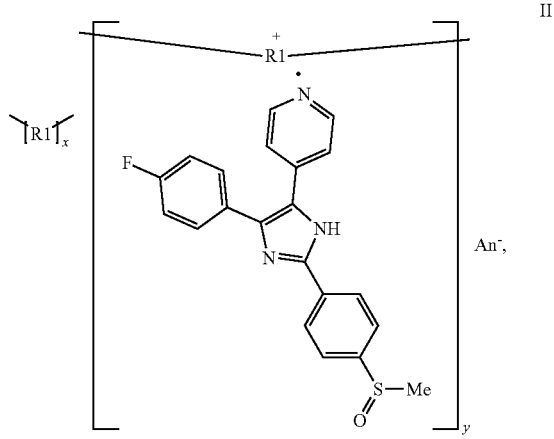

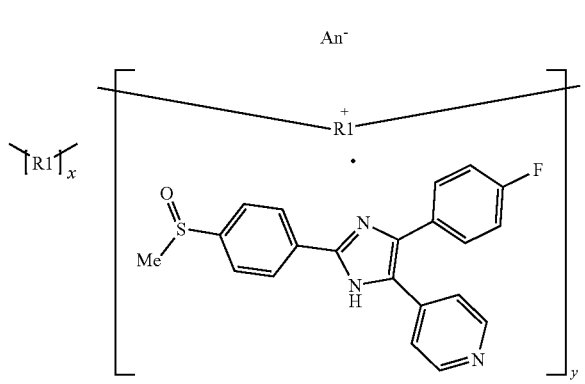

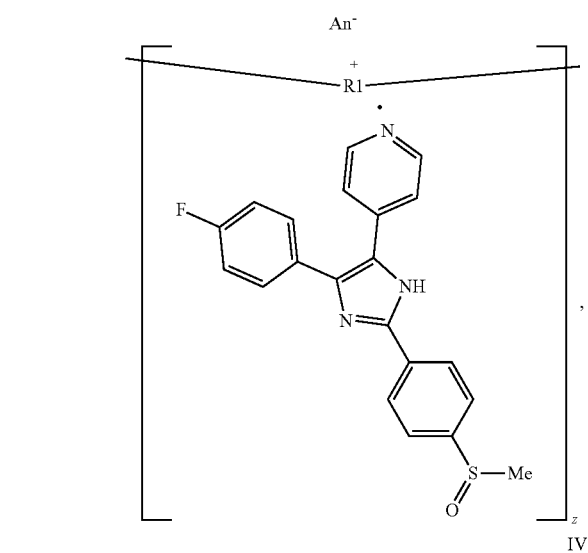

IV

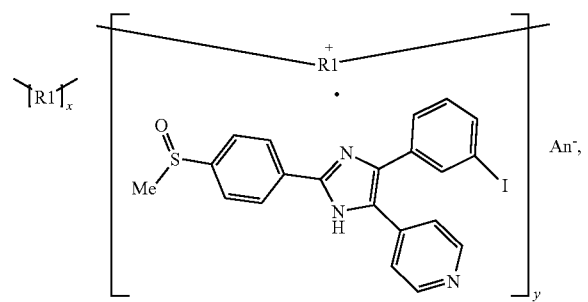

V

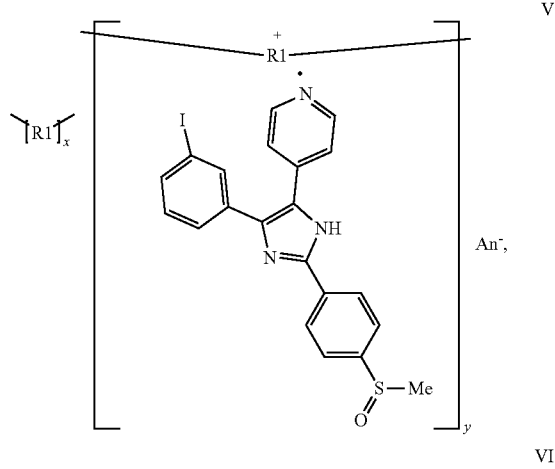

VI

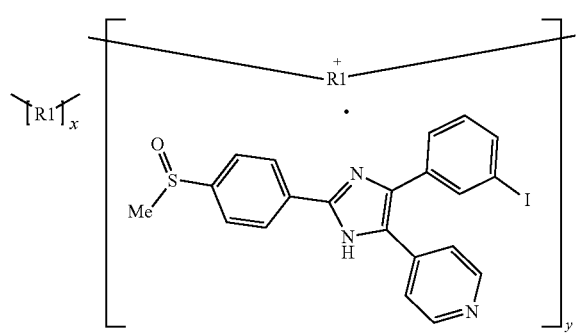

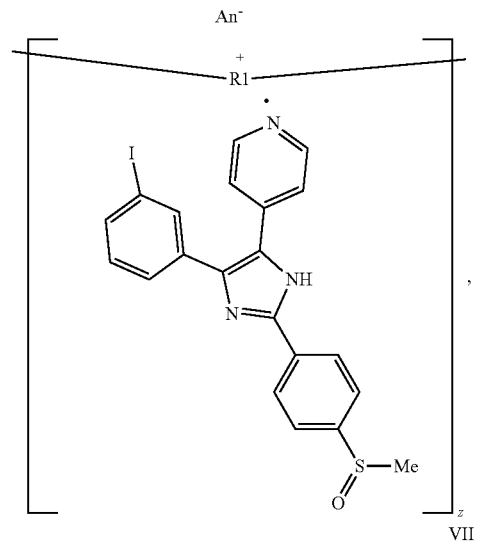

VII 4-(4-fluorophenyl)-2-(4-methylsulfinylphenyl)-5-(4-pyridyl)-1H-imidazole, or a combination thereof;

wherein R1 is a protonated structural unit of a basic water-soluble polymer;

wherein the basic, water-soluble polymer is polyethylenimine, a copolymer of polyethylenimine, polyvinylpyridine, a copolymer of polyvinylpyridine, polyvinylimidazole, a copolymer of polyvinylimidazole, polyvinyltriazole, a copolymer of polyvinyltriazole, chitosan, a derivative of chitosan, carboxymethyl cellulose salts, polyacrylic acid salts, a copolymer of polyacrylic acid salt, polymethacrylic acid, a copolymer of polymethacrylic acid, polymethylmethacrylic, or a copolymer of polymethylmethacrylic;

wherein the drug has a basic moiety that conjugates with the protonated structural unit of the water-soluble polymer;

wherein x, y and z are integers having a value of at least 1; and wherein the composition is administered intraperitoneally to the patient during a surgical procedure, minimally invasive procedure, or diagnostic procedure.

17. The method of claim 16, wherein the composition further comprises a pharmaceutically acceptable carrier, solvent or excipient.

18. The method of claim 16, wherein the composition is in liquid form.

19. The method of claim 18, wherein the composition is administered via injection into the patient.

* * * * *